US006281226B1

(12) United States Patent
Berry et al.

(10) Patent No.: US 6,281,226 B1
(45) Date of Patent: Aug. 28, 2001

(54) PLEUROMUTILIN DERIVATIVES AS ANTIMICROBIALS

(75) Inventors: Valerie Berry, Chester Springs, PA (US); Steven Dabbs, Harlow (GB); Colin Henry Frydrych, Sawbridgeworth (GB); Eric Hunt, Great Dunmow (GB); Francis Dominic Sanderson, Harlow (GB); Gary Woodnutt, Chester Springs, PA (US)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/530,446

(22) PCT Filed: Oct. 27, 1998

(86) PCT No.: PCT/GB98/03211

§ 371 Date: Apr. 27, 2000

§ 102(e) Date: Apr. 27, 2000

(87) PCT Pub. No.: WO99/21855

PCT Pub. Date: May 6, 1999

(30) Foreign Application Priority Data

Oct. 29, 1997 (GB) .................................................. 9722817
Jun. 25, 1998 (GB) .................................................. 9813689

(51) Int. Cl.$^7$ ........................ A61K 31/439; C07D 453/02
(52) U.S. Cl. ........................ 514/305; 546/133; 546/112; 546/183; 548/452; 514/299; 514/412; 514/413
(58) Field of Search ..................... 514/299, 305, 514/325, 412, 413, 428; 546/112, 133, 183, 225, 221, 239; 548/452, 528

(56) References Cited

U.S. PATENT DOCUMENTS

| 4,060,542 | 11/1977 | Riedl . |
| 4,278,674 | 7/1981 | Egger et al. . |
| 4,428,953 | * 1/1984 | Berner et al. ..................... 424/263 |
| 4,675,330 | 6/1987 | Berner et al. . |

FOREIGN PATENT DOCUMENTS

| 0 013 768 | 12/1979 | (EP) . |
| 2 025 930 | 6/1978 | (GB) . |
| WO 97/25309 | 7/1997 | (WO) . |

* cited by examiner

*Primary Examiner*—Charanjit S. Aulakh
(74) *Attorney, Agent, or Firm*—Linda E. Hall; Stephen A. Venentianer; Charles M. Kinzig

(57) ABSTRACT

The present invention relates to pleuromutilin derivatives, to processes for their preparation, to pharmaceutical compositions containing them and to their use in medical therapy, particularly antibacterial therapy.

15 Claims, No Drawings

PLEUROMUTILIN DERIVATIVES AS ANTIMICROBIALS

The present invention relates to novel compounds, to processes for their preparation, to pharmaceutical compositions containing them and to their use in medical therapy, particularly antibacterial therapy.

Pleuromutilin, the compound of formula (A), is a naturally occurring antibiotic which has antimycoplasmal activity and modest antibacterial activity. It has been shown that the antimicrobial activity can be improved by replacing the glycolic ester moiety at position 14 by an R—X—CH$_2$CO$_2$— group, where R is an aliphatic or aromatic moiety and X is O, S, or NR' (H Egger and H Reinshagen, J Antibiotics, 1976, 29, 923). Tiamulin, the compound of formula (B), which is used as a veterinary antibiotic, is a derivative of this type (G Hogenauer in Antibiotics, Vol. V, part 1, ed. F E Hahn, Springer-Verlag, 1979, p.344).

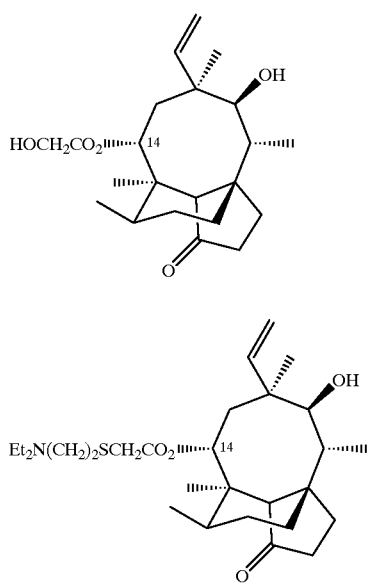

In this application, the non-conventional numbering system which is generally used in the literature (G Hogenauer, loc.cit.) is used.

WO 97/25309 (SmithKline Beecham) describes further modification of the acyloxy group, disclosing 14-O-carbamoyl derivatives of mutilin or 19, 20-dihydromutilin, in which the N-atom of the carbamoyl group is unsubstituted, mono- or di-substituted.

WO 98/05659 (SmithKline Beecham) discloses 14-O-carbamoyl derivatives of mutilin or 19, 20-dihydromutilin, in which the N-atom of the carbamoyl group is acylated by a group which includes an azabicyclic moiety.

WO 98/14189 (SmithKline Beecham. International Publication Date Apr. 9, 1998) discloses the use of the topical antibacterial agent mupirocin for treating bacterial infections associated with the colonisation of the nasopharynx by pathogenic organisms, in particular, the prophylatic treatment of recurrent sinusistis and recurrent otitis media. especially with novel spray or cream formulations adpated for administration to the nasopharynx. In addition, Nsouli (Annals of Allergy, Asthma and Immunology, January 1996, 76(1), 117) has described a clinical study involving the use of a 0.2% aqueous solution of mupirocin in reducing the attacks of sinusitis.

We have now found that further novel pleuromutilin derivatives have improved antimicrobial properties.

Accordingly, the present invention provides a compound of general formula (IA) or (EB):

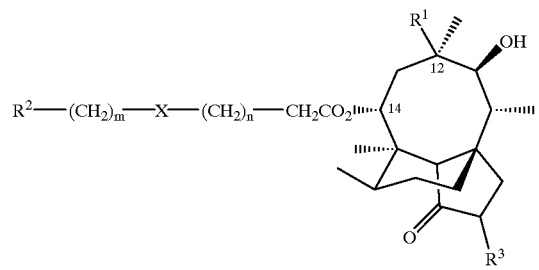

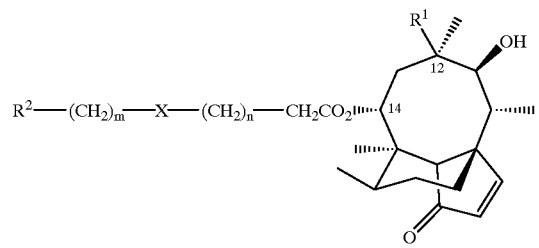

in which:
each of n and m is independently 0, 1 or 2;
X is selected from —O—, —S—, —S(O)—, —SO$_2$—, —CO.O—, —NH—, —CONH—, —NHCONH— and a bond;
$R^1$ is vinyl or ethyl;
$R^2$ is a non-aromatic monocyclic or bicyclic group containing one or two basic nitrogen atoms and attached through a ring carbon atom;
$R^3$ is H or OH; or the moiety $R^2(CH_2))_mX(CH_2)_nCOO$ at position 14 of (IA) or (IB) is replaced by $R^aR^bC$=CHCOO in which one of $R^a$ and $R^b$ is hydrogen and the other is $R^2$ or $R^a$ and $R^b$ together form $R^2$, or
a pharmaceutically acceptable salt thereof.

When $R^2$ is monocyclic, it typically contains from 4 to 8 ring atoms, and, when bicyclic, it typically contains from 5 to 10 ring atoms in each ring, and is optionally substituted on carbon by up to 3 substituents. Suitable substituents include alkyl, alkyloxy, alkenyl and alkenyloxy, each of which may be carried by either a bridgehead or a non-bridgehead carbon atom. In addition, the or each nitrogen atom may be substituted by oxygen, to form an N-oxide, or by mono- or dialkyl, in which case it will be appreciated that a quaternary cation can be formed. The counterion may be a halide ion such as chloride or bromide, preferably chloride. The aza ring system additionally may contain one or more double bonds.

Representative bicyclic and monocyclic groups for $R^2$ include piperidinyl, pyrrolidyl, quinuclidinyl, azabicyclo[2.2.1]heptyl, azabicyclo[4,3,0]nonyl, azabicyclo[3.2.1]octyl, azabicyclo[3,3,0]octyl, azabicyclo[2.2.2]octyl, azabicyclo[3.2.1]octenyl, azabicyclo[3.3.1]nonyl and azabicyclo[4.4.0]decyl, all of which may be substituted or unsubstituted. Preferred examples for $R^2$ include quinuclidinyl.

The compounds of formula (IA) in which $R^3$ is hydroxy have the (2S) configuration at the carbon bearing this hydroxy group.

Preferably, n is 0. Preferably, m is 0 or 1.

Preferred compounds are those of formula (IA).

Alkyl and alkenyl groups referred to herein include straight and branched groups containing up to six carbon atoms and are optionally substituted by one or more groups selected from the group consisting of aryl, heterocyclyl, $(C_{1-6})$alkoxy, $(C_{1-6})$alkylthio, aryl$(C_{1-6})$alkoxy, aryl$(C_{1-6})$alkylthio, amino, mono- or di-$(C_{1-6})$alkylamino, cycloalkyl, cycloalkenyl, carboxy and esters thereof, amides of carboxy, ureido, carbamimidoyl (amidino), guanidino, alkyl-sulfonyl, amino-sulfonyl $(C_{1-6})$acyloxy, $(C_{1-6})$acylamino, azido, hydroxy, and halogen.

Cycloalkyl and cycloalkenyl groups referred to herein include groups having from three to eight ring carbon atoms and are optionally substituted as described hereinabove for alkyl and alkenyl groups.

When used herein, the term "aryl" means single and fused rings suitably containing from 4 to 7, preferably 5 or 6, ring atoms in each ring, which rings may each be unsubstituted or substituted by, for example, up to three substituents. A fused ring system may include aliphatic rings and need include only one aromatic ring. Representative aryl groups include phenyl and naphthyl such as 1-naphthyl or 2-naphthyl.

Suitably any aryl group, including, phenyl and naphthyl, may be optionally substituted by up to five, preferably up to three substituents. Suitable substituents include halogen, $(C_{1-6})$alkyl, aryl, aryl$(C_{1-6})$alkyl, $(C_{1-6})$alkoxy, $(C_{1-6})$alkoxy $(C_{1-6})$alkyl, halo$(C_{1-6})$alkyl, aryl$(C_{1-6})$alkoxy, hydroxy, nitro, cyano, azido, amino, mono- and di-N-$(C_{1-6})$ alkylamino, acylamino, arylcarbonylamino, acyloxy, carboxy, carboxy salts, carboxy esters, carbamoyl, mono- and di-N-$(C_{1-6})$alkylcarbamoyl, $(C_{1-6})$alkoxycarbonyl, aryloxycarbonyl, ureido, guanidino, sulphonylamino, aminosulphonyl, $(C_{1-6})$alkylthio, $(C_{1-6})$alkyl sulphinyl, $(C_{1-6})$alkylsulphonyl, heterocyclyl and heterocyclyl $(C_{1-6})$ alkyl. In addition, two adjacent ring carbon atoms may be linked by a $(C_{3-5})$alkylene chain, to form a carbocyclic ring.

When used herein the terms "heterocyclyl" and "heterocyclic" suitably include, unless otherwise defined, aromatic and non-aromatic, single and fused, rings suitably containing up to four hetcroatoms in each ring, each of which is selected from oxygen, nitrogen and sulphur, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring.

Preferably substituents for a heterocyclyl group are selected from halogen, $(C_{1-6})$alkyl, aryl$(C_{1-6})$alkyl, $(C_{1-6})$ alkoxy, $(C_{1-6})$alkoxy$(C_{1-6})$alkyl, halo$(C_{1-6})$alkyl, hydroxy, amino, mono- and di-N-$(C_{1-6})$alkyl-amino, acylamino, carboxy, carboxy salts, carboxy esters, carbamoyl, mono- and di-N-$(C_{1-6})$alkylcarbonyl, aryloxycarbonyl, $(C_{1-6})$ alkoxycarbonyl$(C_{1-6})$alkyl, aryl, oxy groups, ureido, guanidino, sulphonylamino, aminosulphonyl, $(C_{1-6})$ alkylthio, $(C_{1-6})$alkylsulphinyl, $(C_{1-6})$alkylsulphonyl, heterocyclyl and heterocyclyl$(C_{1-6})$alkyl.

Depending on the position of attachment of substituents, two or more diastereoisomers may be possible. In that situation the present invention includes the individual diastereoisomers and mixtures thereof.

Preferred examples of compounds of the invention include:

Mutilin 14-(quinuclidin-4-yl-sulfanyl)-acetate;

Mutilin 14-(quinuclid-4-ylmethylsulfanyl)-acetate;

Mutilin-14-(1-methylpiperid-4-ylsulfanyl)-acetate, and

Mutilin 14-(exo-8-methyl-8-azabicyclo[3.2.1]oct-3-ylsulfanyl)-acetate.

The compounds of this invention may be in crystalline or non-crystalline form, and, if crystalline, may optionally be solvated, especially hydrated. This invention includes within its scope stoichiometric hydrates as well as compounds containing variable amounts of water.

The compounds according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight.

The compounds of the invention may be in the form of free bases or acid addition salts. Compounds carrying a carboxy substituent may be in the form of zwitterions, or alkali metal salts (of the carboxy group). Pharmaceutically acceptable salts are preferred.

Pharmaceutically acceptable acid-addition salts include those described by Berge, Bighley, and Monkhouse, *J. Pharm. Sci.*, 1977, 66, 1–19. Suitable salts include the hydrochloride, maleate, and methanesulphonate; particularly the hydrochloride.

Compounds of the present invention may be readily prepared form available starting materials by adapting synthetic processes well known in the art.

Accordingly, in a first aspect, the present invention provides a process for preapring a compound of formula (I) which comprises reacting a compound of formula (IIA) or (IIB):

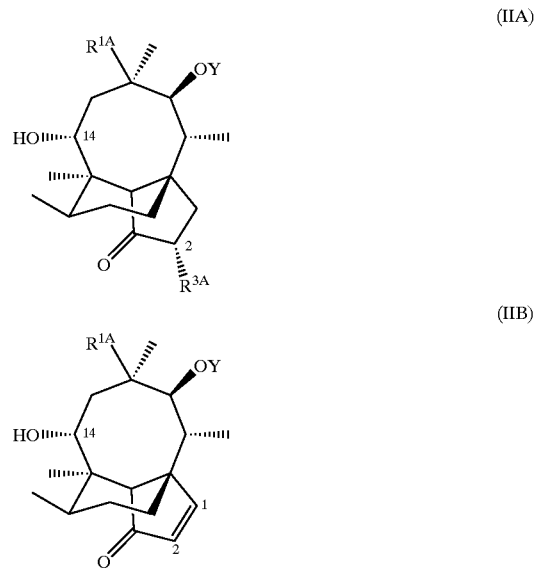

in which Y is hydrogen or a removable hydroxy-protecting group, and $R^{1A}$ and $R^{3A}$ are $R^1$ and $R^3$ are as defined for formulae (IA) and (IB) or groups convertible to $R^1$ and $R^3$, with an active derivative of a carboxylic acid of formula (III):

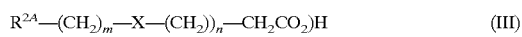

where $R^{2A}$ is $R^2$ as defined for formulae IA and IB or a group convertible to $R^2$, under ester forming conditions and, where required or desired, converting Y to hydrogen, converting an $R^{1A}$, $R^{2A}$ or $R^{3A}$ group to a $R^1$, $R^2$ or $R^3$ group, and/or converting one $R^1$, $R^2$ or $R^3$ group to another $R^1$, $R^2$ or $R^3$ group.

Conventional methods for ester formation are described in the literature, for example in *Comprehensive Organic Functional Group Transformations*, Vol. 5, ed. C J Moody, p. 123–130, Elsevier Scientific, Oxford, 1995. The active derivative used as an acylating agent may be for example an acid chloride, acid bromide, a mixed anhydride, or an N-acyl-imidazole. The preferred agent is an acid chloride. General methods for forming such acylating agents are described in the chemical literature (see I O Sutherland, *Comprehensive Organic Chemistry*, Vol. 2, ed. I O Sutherland, pages 875–883 (Pergamon Press, Oxford, 1979), and references therein).

The ester-forming reaction can be carried out in the presence of an organic base, an inorganic base, or an acid. Organic bases include pyridine, 2,6-lutidine, triethylamine, and N,N-dimethylaniline. Inorganic bases include sodium hydride, lithium hydride, potassium carbonate, lithium hexamethyldisilazide, and sodium hexamethyldisilazide. Acids include p-toluenesulphonic acid, benzene sulphonic acid, and sulphuric acid. Optionally, when the reaction is carried out in the presence of a base, an acylation catalyst (G Hofle and W Steglich, *Synthesis*, 1972, 619) such as 4-dimethyamino-pyridine or 4-pyrrolidino-pyridine may also be added to the reaction mixture. Solvents for the ester forming reaction include tetrahydrofuran, 1,4-dioxane, acetonitrile, N,N-dimethylformamide, diethyl ether, dichloromethane, and chloroform. A preferred solvent is tetrahydrofuran.

Useful methods for acylating the 14-hydroxyl in the present invention include the use of the following: acid chloride in N,N-dimethylformamide at elevated temperature (e.g. 100° C. to 120° C.), acid chloride in the presence of an organic base (e.g. pyridine, 2,6-lutidine, 2,4,6-collidine, di-iso-propylethylamine) or an inorganic base (e.g. sodium or lithium hexamethyldisilazide); carboxylic acid in the presence of dicyclohexylcarbodiimide and an acylation catalyst (e.g. 4-dimethylamino-pyridine, 4-pyrrolidino-pyridine); a mutilin 14-chloroformate derivative plus carboxylic acid, tertiary base (e.g. triethylamine. di-iso-propylethylamine), and an acylation catalyst (e.g. 4-dimethylamino-pyridine, 4-pyrrolidino-pyridine).

Conversions of an $R^{1A}$, $R^{2A}$ or $R^{3A}$ group to a $R^1$, $R^2$ or $R^3$ group typically arise when a protecting group is needed during the above coupling reaction or during the preparation of the reactants by the procedures described below. Interconversion of one $R^1$, $R^2$ or $R^3$ group to another typically arises when one compound of formula IA/B is used as the immediate precursor of another compound of formula IA/B or when it is easier to introduce a more complex or reactive substituent at the end of a synthetic sequence.

Preferably Y is a hydroxyl protecting group such as an acyl group, for example so that —OY is trifluoroacetyl or dichloroacetyl. When the intended $R^3$ is also hydroxyl, then $R^{3A}$ is also preferably acyloxy, for example acetyl or dichloroacetyl. Hydroxyl groups at positions 11 and 2 (as groups OY and $R^{3A}$) may be protected using, for example, dichloroacetic anhydride and pyridine in tetrahydrofuran or N-trifluoroacetyl-imidazole in tetrahydrofuran at 0° C. After the reaction with the derivative of acid III is complete the protecting acyl groups may be removed to restore the hydroxyl groups by hydrolysis e.g. using NaOH in MeOH.

It may also be necessary to protect substituent groups in the acid component (III) prior to reaction with the the compound of formulae (IIA) or (IIB), for example protecting N atoms with alkoxycarbonyl, for example t-butoxycarbonyl.

Suitable hydroxy, carboxy and amino protecting groups are those well known in the art and which may be removed under conventional conditions and without disrupting the remainder of the molecule. A comprehensive discussion of the ways in which hydroxy, carboxy and amino groups may be protected and methods for cleaving the resulting protected derivatives is given in for example "Protective Groups in Organic Chemistry" (T. W. Greene, Wiley-Interscience, New York, 2nd edition, 1991). Particularly suitable hydroxy protecting groups include, for example, triorganosilyl groups such as, for instance, trialkylsilyl and also organocarbonyl and organooxycarbonyl groups such as, for instance, acetyl, allyloxycarbonyl, 4-methoxybenzyloxycarbonyl and 4-nitrobenzyloxycarbonyl. Particularly suitable carboxy protecting groups include alkyl and aryl groups, for instance methyl, ethyl and phenyl. Particularly suitable amino protecting groups include alkoxycarbonyl, 4-methoxybenzyloxycarbonyl and 4-nitrobenzyloxycarbonyl.

$R^{1A}$ is typically the $R^1$ group vinyl, and this may be converted to the alternative $R^1$ ethyl group by hydrogenating the vinyl group to form an ethyl group, typically by hydrogenation over a palladium catalyst (e.g. 10% palladium-on-carbon) in a solvent such as ethyl acetate, ethanol, dioxane, or tetrahydrofuran.

$R^{3A}$ is typically hydrogen or protected hydroxyl, such as acyloxy. After the coupling reaction, protecting acyl groups may be removed to restore the hydroxyl groups by hydrolysis e.g. using NaOH in MeOH.

Alternatively a compound of formula (IA) in which $R^3$ is hydrogen may be prepared by treating a compound of formula (IIC):

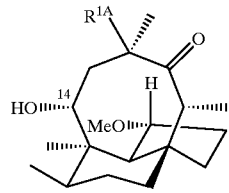

(IIC)

where $R^{1A}$ is as defined for formulae (IIA) and (IIB),
with an active derivative of the acid of formula (III) under ester forming conditions, and
then treating the product with an acid, and, where required or desired,
converting an $R^{1A}$ or $R^{2A}$ group to a $R^1$ or $R^2$ group, and/or
converting one $R^1$ or $R^2$ group to another $R^1$ or $R^2$ group.

The acid treatment indicated above converts the epi-mutilin configuration of formula (IIC) to the usual mutilin nucleus of formula (IIA). Typically this conversion is carried out by treatment with conc. HCl or Lukas reagent (conc. HCl saturated with $ZnCl_2$) in dioxane.

As in formulae (IIA) and (IIB), $R^{2A}$ is typically the $R^2$ group vinyl, and this may be converted to the alternative $R^2$ group by hydrogenating the vinyl group to form an ethyl group. Also it may again be necessary to protect substituent groups in the derivative of acid component (III) prior to reaction, for example protecting N atoms with, for example, t-butoxycarbonyl.

In cases where the intermediate of formula (IIA) and (IIB) (such as Y=acetyl) are used, a base-labile protecting group may conveniently be removed at the same time as the group Y is deprotected. In cases when the intermediate of formula (IIC) is used, an acid-labile protecting group may conveniently be removed at the same time as the acid treatment that converts the epi-mutilin configuration into the desired configuration of the compounds of the invention.

The compounds of formulae (IIA), (IIB) and (IIC) may be prepared from compounds of formulae (IV) and (V)

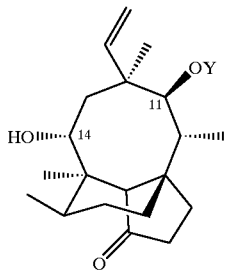

(IV)

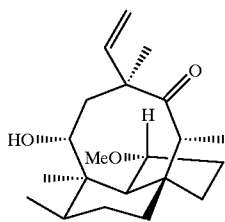

(V)

Suitable compounds as formula (IV) include 11-O-acyl mutilin derivatives, e.g. mutilin 11-acetate (A J Birch. C W Holzapfel, R W Richards, Tetrahedron (Suppl.), 1966, 8, Part II, 359) or mutilin 11-dichloroacetate or mutilin 11-trifluoroacetate. Formula (V) is (3R)-3-deoxo-11-deoxy-3-methoxy-11-oxo-4-epi-mutilin (H Berner, G Schulz and H Schneider, Tetrahedron, 1980, 36, 1807).

Compounds (IV) and (V) are effectively the compounds of formula (IIA) and (IIC) respectively in which $R^{1A}$ is vinyl and $R^{3A}$ is hydrogen (compound IIA). They may be converted into the corresponding compounds in which $R^{1A}$ is ethyl by hydrogenation, typically by hydrogenation over a palladium catalyst (e.g. 10% palladium-on-carbon) in a solvent such as ethyl acetate, ethanol, dioxane, or tetrahydrofuran.

Copmpounds of formula (IIA) in which $R^{3A}$ is hydroxyl may be obtained by first preparing 2-hydroxymethylene mutilin from a compound of formula (IV). Using procedures based on that described by A. J. Birch, C. W. Holzapfel and R. W. Rickards (Tet (Suppl) 1996 8 part III 359), a compound of formula (IV) in toluene and methyl formate is treated with sodium methoxide and stirred under argon. The product is a mixture of the desired 2-hydroxymethylene compound and corresponding compounds substituted by formate at position 11 (if OY is OH) and /or position 14. The formate groups may be removed when desired by treatment with potassium hydroxide in methanol.

The product mixture may however be used directly to prepare 2-diazo-mutilin derivatives using the method described by H Berner, G Schulz, and G Fisher, Monatsh. Chem., 1981, 112, 1441, for example reacting a solution of a 2-hydroxymethylene-mutilin and the formate derivatives in dichloromethane at −10 ° C. under argon with tosylazide and triethylamine. Removal of the formate groups as described above leaves 2-diazo-mutilin. which may be reacted with a carboxylic acid to give a 2-acyloxy-mutilin, effectively a compound of formula (IIA) in which $R^{3A}$ is protected hydroxyl. Suitably reaction with dichloroacetic acid gives 2-dichloroacetoxy-mutilin, which can be deprotected as described above to provide 2-OH. preferably after coupling with the derivative of acid (III). This reaction produces (2S)-2-hydroxy derivatives.

Compounds of formula (IIB) are either 1,2-didehydro-mutilin or obtainable therefrom by manipulation of OY and $R^{1A}$ as described above. 1,2-Didehydro-mutilins may be prepared using the method described by G Schulz and H Berner in Tetrahedron, 7, 1984, 40, 905.

The above described modifications to the mutilin nucleus may also be carried out after coupling of compounds of formula (IIA) and (IIC) where $R^{3A}$ is hydrogen (i.e. based on mutilin an d epi-mutilin) with the active derivative of acid (III).

In another aspect, the present invention provides a method for preparing compounds of the invention in which X is O, S, NH, CO.O or CONH which comprises reacting a compound of formula VIA o r VIB

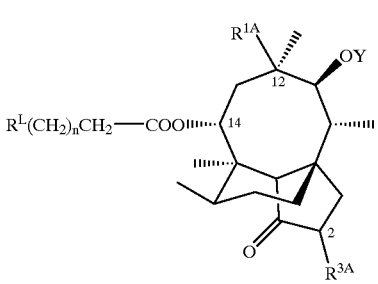

VIA

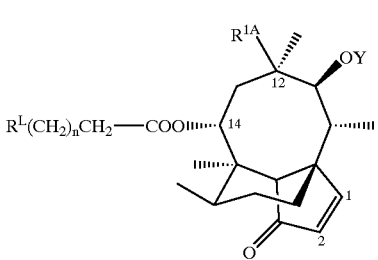

VIB where Y is hydrogzen or a removable hydroxy-protecting, group. and $R^{1A}$ and $R^{3A}$ are $R^{1}$ and $R^{3}$ as defined for formulae IA and IB or groups convertible to $R^{1}$ and $R^{3}$, n is as defined for formulae IA and IB, and $R^{L}$ is a leaving group or OH or $NH_2$, with a compound of formula (VII):

$$R^{2A}—(CH_2)_m—XH \qquad (VII)$$

where $R^{2A}$ is $R^{2}$ as defined for formulae (IA) and (IB) or a group convegible to $R^{2}$, and X and m are as defined for formulae IA and IB, or when X is CO.O with an active derivative of the acid of formula (VII), by one of the procedures set out below, and where required or desired converting Y to hydrogen, converting an $R^{1A}$ or $R^{3A}$ group to an $R^{1}$, $R^{2}$ or $R^{3}$ group, and/or converting one $R^{1}$, $R^{2}$ or $R^{3}$ group to another $R^{1}$, $R^{2}$ or $R^{3}$ group.

As in the method discussed above startin from compounds (IIA/B/C), preferably Y is a hydroxyl protecting group such as an acyl group, for example so that —OY is trifluoroacetyl or dichloroacetyl. When the intended $R^3$ is also hydroxyl then $R^{3A}$ is also preferably acyloxy, for example acetyl or dichloroacetyl.

It may also be necessary to protect substituent groups in the compound of formula (VII) prior to reaction with the compound (VIA) or (VIB), for example protecting N atoms with alkoxycarbonyl, for example t-butoxycarbonyl.

Suitable hydroxy, carboxy and amino protecting croups are those well known in the art and are discussed above.

$R^{1A}$ is typically the $R^1$ group vinyl, and this may be converted to the alternative $R^1$ ethyl group by hydrogenating the vinyl group to form an ethyl group, typically by hydrogenation over a palladium catalyst (e.g. 10% palladium-on-carbon) in a solvent such as ethyl acetate, ethanol, dioxane, or tetrahydrofuran.

$R^{3A}$ is typically hydrogen or protected hydroxyl, such as acyloxy. After the coupling reaction, protecting acyl groups may be removed to restore the hydroxyl groups by hydrolysis e.g. using NaOH in MeOH.

Procedures for coupling the group $R^L(CH_2)_nCH_2CO.O$— with compond $R^{2A}$—$(CH_2)_m$—XH include the following:

(a) when $R^L$ is a leaving group, such as 4-MeC$_6$H$_4$SO$_2$O, MeSO$_2$O, F$_3$CSO$_2$O, Br or Cl, and X is O, S or NH:

(i) where X=O, the alcohol $R^2$—$(CH_2)_m$—OH may be converted into the alkoxide by reaction with an inorganic base, such as sodium hydride, lithium hydride, sodium hexamethyldisilazide, or lithium hexamethyldisilazide, in a non-hydroxylic solvent, such as N,N-dimethylformamide or tetrahydrofuran, prior to reaction with the compound of formula VIA/B;

(ii) where X=S, the thiol $R^2$—$(CH_2))_m$—SH may be reacted with the compound of formula VIA/B in the presence of an inorganic base, such as sodium methoxide, sodium ethoxide, sodium hydride, sodium hexamethyldisilazide, or lithium hexamethyldisilazide, in a solvent such as 2-propanol, ethanol, methanol, N,N-dimethylformamide, or tetrahydro furan.

(iii) where X=NH, the amine $R^2$—$(CH_2)_m$—NH$_2$ may be reacted with the compound of formula VIA/B in a solvent such as N,N-dimethylformamide or tetrahydrofuran, optionally in the presence of a base such as potassium carbonate, pyridine, N,N-di-(iso-propyl)-ethylamine, or triethylamine.

(b) when X is CONH, a compound of formula VIA in which $R^L$ is amino may be reacted with a compound of formula $R^{2A}$—$(CH_2)_m$—CO$_2$H, or an acylating agent derived therefrom, using one of the general methods for amide formation that are described in the chemical literature. General methods for amide formation are described by B C Challis and J A Challis in *Comprehensive Organic Chemistry*, Vol. 2. ed. I O Sutherland, pages 959–964 (Pergamon Press, Oxford, 1979).

(c) when X is CO.O, a compound of formula VIA/B in which $R^L$ is hydroxy may be reacted with an acylating agent derived from a compound of formula $R^{2A}$—$(CH_2)_m$—CO$_2$H, using one of the general methods that are described in the chemical literature, for example treating the acid with oxalyl chloride and reacting with $R^L$=hydroxy in a suitable solvent such as DMF.

Alternatively the above reactions may be carried out using a compound of formula (VIC):

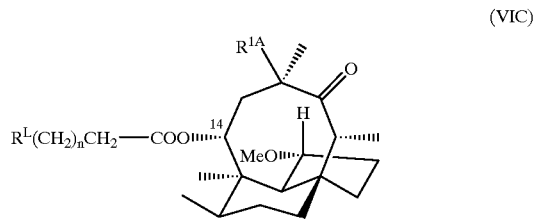

(VIC)

where Y and $R^{1A}$ are as defined for formulae IIA and IIB and $R^L$ is as defined for formulae (VIA) and (VIB) with the compound (VII) by the procedures (a), (b) or (c) set out above,
and then
treating the product with an acid,
and where required or desired
converting an $R^{1A}$ or $R^{2A}$ group to a $R^1$ or $R^2$ group, and/or converting one $R^1$ or $R^2$ group to another $R^1$ or $R^2$ group.

As mentioned previously, the acid treatment indicated above converts the epi-mutilin configuration of formula (VIC) to the usual mutilin nucleus of formula (VIA). Typically this conversion is carried out by treatment with conc. HCl or Lukas reagent (conc. HCl saturated with ZnCl$_2$) in dioxane.

As in formulae (VIA) and (VIB), $R^{1A}$ is typically the $R^1$ group vinyl, and this may be converted to the alternative $R^1$ group by hydrogenating the vinyl group to form an ethyl group. Also it may again be necessary to protect substituent groups in the compound (VII) prior to reaction, for example protecting N atoms with alkoxycarbonyl, for example t-butoxycarbonyl.

The compounds of formulae (VIA), (VIB) and (VIC) may be prepared by reacting the corresponding compounds of formula (IIA), (IIB) and (IIC) by conventional methodology to introduce acyl groups substituted by hydroxyl or amine or a leaving group.

Reference is directed to the preparation of the chloride and tosylate by K Riedl in *J. Antibiotics*, 1976, 29, 132; and the tosylate and mesylate described by H Egger and H Reinshagen in *J. Antibiotics*. 1976, 29, 915; starting from pleuromutilin or 19,20-dihydro-pleuromutilin (n=0) . Also compounds where $R^L$ is chloro or bromo may be prepared by reacting Br(CH$_2$))$_n$(CH$_2$)COOCl or Cl(CH$_2$)$_n$(CH$_2$)COOCl with compounds IV and V above. It will be appreciated that when n=0, compounds where $R^L$ is hydroxy are pleuromutilin and 19,20-dihydro-pleuromutilin. Compounds where $R^L$ is NH$_2$ may be prepared from the compound where $R^L$ is a leaving group, for example treating a tosylate with sodium azide, followed by treatment with triphenyl phosphine and a base.

Compounds of formula (IA) wherein X is S(O) or SO$_2$ may be obtained by preparing the corresponding compound in which X=S and treating it with an oxidising agent; for example, 3-chloroperoxybenzoic acid in chloroform, or catalytic osmium tetroxide plus N-methylmorpholine N-oxide in tetrahydrofuran and tertiary-butanol.

It will be appreciated that it is also possible to carry out the reaction of the compounds VIA/B/C with compound VII with the substituents reversed, i.e. with —CH$_2$(CH$_2$)$_n$XH as a 14-mutilin substituent and $R^L$ on the $R^{2A}$—(CH$_2$)$_m$— residue. For example 22-deoxy-22-sulfanyl-pleuromutilin (U.S. Pat. No. 4,130,709) may be reacted with a compound of formula $R^{2A}$—$(CH_2)_m$— $R^L$, where $R^L$ is a leaving group, such as 4-MeC$_6$H$_4$SO$_2$O, MeSO$_2$O, CF$_3$SO$_2$O, or Cl, in the presence of an inorganic base, such as sodium methoxide, sodium ethoxide, or sodium hydride, in a solvent such as 2-propanol, ethanol, methanol, or tetrahydrofuran.

The compounds (III) and (VII) are commercially available or may be formed by conventional methodology from compounds that are commercially available compounds or described in the literature.

Where intermediates disclosed for the above processes are novel compounds, they also form part of this invention.

The compounds of the present invention may contain a chiral centre, and therefore the products of the above processes may comprise a mixture of diastereoisomers or a single diastereoisomer. A single diastereoisomer may be prepared by separating such a mixture of diastereoisomers which has been synthesised using a racemic starting material, or by synthesis using an optically pure starting material.

The products of the processes of this invention may be in crystalline or non-crystalline form, and, if crystalline, may optionally be hydrated or solvated. When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be present in the crystalline product. This invention includes within its scope stoichiometric hydrates as well as compounds containing variable amounts of water that may be produced by processes such as lyophilisation.

The compounds obtained according to the processes of the invention are suitably worked up to a substantially pure form, for example at least 50% pure, suitable at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

The present invention also includes pharmaceutically acceptable salts and derivatives of the compounds of the invention. Salt formation may be possible when one of the substituents carries an acidic or basic group. Salts may be prepared by salt exchange in conventional manner Acid-addition salts may be pharmaceutically acceptable or non-pharmaceutically acceptable. In the latter case, such salts may be useful for isolation and purification of the compound of the invention, or intermediates thereto, and will subsequently be converted into a pharmaceutically acceptable salt or the free base. Pharmaceutically acceptable acid-addition salts include those described by Berge, Bighley, and Monkhouse, *J. Pharm. Sci.*, 1977, 66, 1–19. Suitable salts include the hydrochloride, maleate, and methanesulphonate; particularly the hydrochloride.

It will also be understood that where the compound of the invention contains a free carboxy moiety, it can form a zwitterion.

The compounds of the present invention and their pharmaceutically acceptable salts or derivatives have antimicrobial properties and are therefore of use in therapy, in partiuclar for treating microbial infections in animals, especially mammals, including humans, in particular humans and domesticated animals (including farm animals). The compounds may be used for the treatment of infections caused by, for example, Gram-positive and Gram-negative bacteria and mycoplasmas, including, for example, *Staphylococcus aureus, Staphylococcus epidermidis, Enterococcus faecalis, Streptococcus pyogenes, Streptococcus agalactiae, Streptococcus pneumoniae*, Haemophilus sp., Neisseria sp., Legionella sp., Chlamydia sp., *Moraxella catarrhalis, Mycoplasma pneumoniae*, and *Mycoplasma gallisepticum*.

The present invention also provides a method of treating microbial infections in animals. especially in humans and in domesticated mammals, which comprises administering a compound of the invention or a pharmaceutically acceptable salt or derivative or solvate thereof, or a composition according to the invention, to a patient in need thereof.

The invention further provides the use of a compound of the invention or a pharmaceutically acceptable salt or derivative or solvate thereof in the preparation of a medicament for use in the treatment of microbial infections.

Compounds of the present invention may be used to treat skin and soft tissue infections and acne, by topical application. Accordingly, in a further aspect the present invention provides the use of a compound of the invention or a pharmaceutically acceptable salt or derivative or solvate thereof in the preparation of a medicament adapted for topical administration for use in the treatment of skin and soft tissue infections and also in the treatment of acne in humans.

Compounds of the present invention may be also used for the elimination or reduction of nasal carriage of pathogenic bacteria such as *S. aureus. H. influenzae, S. pneumonia* and *M. catarrhalis*, in particular colonisation of the nasospharynx by such organisms, by the administration of a compound of the present invention thereto. Accordingly, in a further aspect, the present invention provides for the use of a compound of the invention or a pharmaceutically acceptable salt or derivative or soivate thereof in the manufacture of a medicament adapted for administration to the nasal cavity, for reducing or eliminating the nasal carriage of pathogenic organisms. Preferably, the medicament is adapted for focussed delivery to the nasopharynx, in particular the anterior nasopharynx.

Such reduction or elimination of nasal carriage is believed to be useful in prophylaxis of recurrent acute bacterial sinusitis or recurrent otitis media in humans, in particular in reducing the number of episodes experienced by a patient over a given period of time or reducing the time intervals between episodes. Accordingly, in a further aspect, the present invention provides for the use of a compound of the invention or a pharmaceutically acceptable salt or derivative or solvate thereof in the manufacture of a medicament adapted for administration to the nasal cavity, for prophylaxis of recurrent acute bacterial sinusitis or recurrent otitis media.

Compounds of the present invention are also useful in treating chronic sinusitis. Accordingly, in a further aspect, the present invention provides for the use of a compound of the invention or a pharmaceutically acceptable salt or derivative or solvate thereof in the manufacture of a medicament, for treating of chronic sinusitis.

The compounds according to the invention may suitably be administered to the patient at a daily dosage of from 1.0 to 50 mg/kg of body weight. For an adult human (of approximately 70 kg body weight), from 50 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

To lessen the risk of encouraging the development of resistant organisms during prophylaxis of recurrent otitis media or recurrent acute bacterial sinusitis, it is preferred to administer the drug on an intermittent, rather than a continual, basis. In a suitable intermittent treatment regimen for prophylaxis of recurrent otitis media or recurrent sinusitis, drug substance is administered on a daily basis, for a small number of days, for instance from 2 to 10, suitably 3 to 8, more suitably about 5 days, the administration then being repeated after an interval, for instance, on a monthly basis over a period of months, for instance up to six months. Less preferably, the drug substance may be administered on a continuing, daily basis, over a prolonged period, for instance several months. Suitably, for prophylaxis of recurrent otitis media or recurrent sinusitis, drug substance is administered once or twice a day. Suitablyv drug substance is administered during the winter months when bacterial infections such as recurrent otitis media and recurrent sinusitis tend to be more prevalent. The drug substance may be administered at a dosage of from 0.05 to 1.00 mg, typically about 0.1 to 0.2mg, in each nostril. once or twice a day.

More generally, the compounds and compositions according to the invention may be formulated for administration in any convenient way for use in human or veterinary medicine, by analogy with other antibiotics.

Accordingly, in a further aspect, the present invention provides a pharmaceutical composition comprising a compound of the invention or a pharmaceutically acceptable salt or derivative or solvate thereof toether with a pharmaceutically acceptable carrier or excipient.

The compounds and compositions according to the invention may be formulated for administration by any route, for example oral, topical or parenteral. The compositions may, for example, be made up in the form of tablets, capsules, powders, granules, lozenges, creams, syrups, sprays or liquid preparations, for example solutions or suspensions, which may be formulated for oral use or in sterile form for parenterai administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrollidone; fillers, for example lactose, sugar, maize-starch, calcium phosphate, sorbitol or glycine; tabletting lubricants, for example magnesium stearate, talc, polyethylene glycol or silica; disintegrants, for example potato starch: and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol, preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, nose drops, nasal sprays, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, ethanol or oleyl alcohol for lotions and aqueous bases for sprays. Such carriers may constitute from about 1% to about 98% by weight of the formulation; more usually they will constitute up to about 80% by weight of the formulation.

Compositions according to the invention intended for topical administration, in addition to the above, may also contain a steroidal anti-inflammatory agent; for example, betamethasone.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilised before being filled into a suitable vial or ampoule, which is then sealed. Advantageously, conventional additives including, for example, local anaesthetics, preservatives, and buffering agents can be dissolved in the vehicle. In order to enhance the stability of the solution, the composition may be frozen after being filled into the vial, and the water removed under vacuum; the resulting dry lyophilised powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

A compound or composition according to the invention is suitably administered to the patient in an antimicrobially effective amount.

A composition according to the invention may suitably contain from 0.001% by weight, preferably (for other than spray compositions) from 10 to 60% by weight, of a compound according to the invention (based on the total weight of the composition), dependin on the method of administration.

When the compositions according to the invention are presented in unit dosage form, for instance as a tablet, each unit dose may suitably comprise from 25 to 1000 mg, preferable from 50 to 500 mg, of a compound according to the invention.

Preferred compositions of the present invention include those adapted for intranasal administration, in particular, those that will reach into the nasopharynx. Such compositions are preferably adapted for focussed delivery to, and residence within, the nasopharynx. The term 'focussed delivery' is used to mean that the composition is delivered to the nasopharynx, rather than remaining within the nares. The term 'residence' within the nasopharynx is used to mean that the composition, once delivered to the nasopharynx, remains within the nasopharynx over a course of several hours, rather than being washed away more or less immediately. Preferred compositions include spray compositions and creams. Representative spray compositions include aqueous compositions, as well as oily compositions which contain amphiphilic agents so that the composition increases in viscosity when in contact with moisture. Creams may also be used, especially creams having a rheology that allows the cream to spread readily in the nasopharynx.

Preferred aqueous spray compositions include, in addition to water, further excipients including a tonicity modifier such as a salt, for instance sodium chloride: preservative, such as benzalkonium salt; a surfactant such as a non-ionic surfactant, for instance a polysorbate; and buffer, such as sodium dihydrogen phosphate; present in low levels, typically less than 1%. The pH of the composition may also be adjusted, for optimum stability of the drug substance during storage. For compounds of the present invention, a pH in the range 5 to 6, preferably about 5.3 to 5.8, typically about 5.5 is optimal Representative oily spray and cream compositions are described in WO 98/14189 (SmithKline Beecham).

Suitably, the drug substance is present in compositions for nasal delivery in between 0.001 and 5%, preferably 0.005 and 3%, by weight of the composition. Suitable amounts include 0.5% and 1% by weight of the composition (for oily compositions and creams) and from 0.01 to 0.2% (aqueous compositions).

Preferably, an aqueous spray composition is used. Such compositions are found to show similar retention in the target area (nasal cavity and nasopharynx) in gamma scintigraphy studies and have superior release rates in synthetic membrane diffusion studies when compared to an oily composition as described in WO 98/14189. In addition, an aqueous base was found to be prefered to an oily base in sensory analysis studies.

Spray compositions according to the present invention may be delivered to the nasal cavity by spray devices well known in the art for nasal sprays, for instance an air lift pump. Prefrrred devices include those which are metered to provide a unit volume of composition prefereably about 100 µl, and optionally adpated for nasal administration by addition of a modified nozzle.

The following Examples illustrate the present invention and particularly the preparative procedures outlined above, by reference to the preparation of specific compounds within the scope of the present invention.

Note on Naming of Pleuromutilin Analogues

In the Examples, compound (a), which in the IUPAC system has the systematic name (1S, 2R, 3S, 4S, 6R, 7R, 8R, 14R)-3,6-dihydroxy-2,4,7,14-tetramethyl-4-vinyl-tricyclo [5.4.3.0$^{1,8}$]tetradecan-9-one, is referred to using the trivial name mutilin and with the numbering system described by H Berner, G Schulz, and H Schneider in *Tetrahedron*, 1981, 37, 915–919.

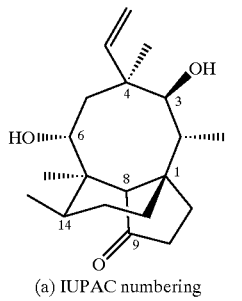
(a) IUPAC numbering

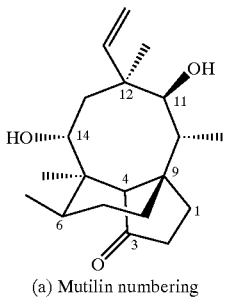
(a) Mutilin numbering

Likewise, compound (b), which has the systematic name (1R, 2R, 4S, 6R, 7R, 8S, 9R, 14R)-6-hydroxy-9-methoxy-2,4,7,14-tetramethyl-4-vinyl-tricyclo[5.4.3.0$^{1,8}$]tetradecan-3-one, is named as (3R)-3-deoxo-11-deoxy-3-methoxy-11-oxo-4-epi-mutilin.

(b)

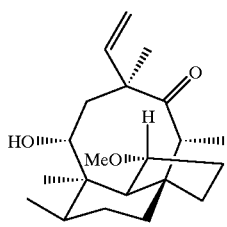

EXAMPLE 1

Mutilin 14-(quinuclidin-4-yl-sulfanyl)-acetate

Quinuclidin-4-thiol hydrobromide (1.9 g, 0.009 mole) (W. Eckhardt and E. A. Grob, *Helvetica Chimica Acta* (1974), 57 (8)m 2339–2345) was added to a stirred solution of sodium ethoxide (1.72 g, 0.0253 mole) in ethanol (50 ml) under argon at room temperature. The mixture was stirred for 10 minutes before adding a solution of mutilin 14-toluenesulfonyloxyacetate (K. Ridel , *J. Antibiotics* (1976), 29m 132–139) (6.23 g. 0.0117 mole) in methyl ethyl ketone (20 ml). The mixture was stirred overnight at room temperature under argon, then concentrated in vactio. The residue was partitioned between dichloromethane and water. The organic layer was washed with water, dried over magnesium sulphate, and concentrated in vacuo. The crude product was purified by chromatography on silica gel eluting with chloroforrn/methanol/35% ammonia solution (19:1:0.1) to give the title compound as a solid 1.8 g (40%): $^1$H NMR (CDCl$_3$) inter alia 0.75 (3H, d, J 6.7 Hz), 0.88 (3H, d, J 7 Hz), 1.25 (3H, s), 1.46 (3H, s), 1.68 (6H, t, J 7.6 Hz), 2.93 (6H, t, J 7.6 Hz), 3.18 (2H, ABq), 3.35 (1H, m), 5.19 (1H, dd, J 17.5 and ), 5.33 (1H, dd), 6.45 (1H, dd, J 17.4 and 11 Hz). MS (EI) m/z 504 (M$^+$).

EXAMPLE 2

Mutilin 14-(quinuclidin-4-yl-sulfanyl)-acetate Hydrochloride

Mutilin 14-(quinuclidin-4-yl-sulfanyl)-acetate (1.0 g) was dissolved in a minimum volume of acetone and a 1M solution of HCl in ether was added. The heterogeneous mixture was concentrated in vacuo. The residue was triturated with ether (20 ml) and 1M HCl/ether (5 ml) to give the title compound as a beige solid (0.94 g); $^1$H NMR (D$_2$O)

inter alia 0.63 (3H, d, J 6 Hz), 0.86 (3H, d, J 6.8 Hz), 1.09 (3H, s), 1.36 (3H, s), 2.05 (6H, m), 3.40 (6H, m), 3.49 (1H, m), 5.10 (2H, m), 5.64 (1H, d, J 8.3 Hz), 6.29 (1H, dd, J 17.4 and 11 Hz). MS (EI) m/z 504 ($M^{+)}$·

EXAMPLE 3

19,20-Dihydromutilin 14-(quinuclidin-4-yl-sulfanyl)-acetate

A solution of mutilin 14-(quinuclidin-4-yl-sulfanyl)-acetate (0.314 g, 0.00063 mole) in ethanol (30 ml) was hydrogenated over 10% Pd—C paste (50% moisture content) at room temperature for 1 hour. The catalyst was filtered off and the filtrate concentrated in vacuo. The residue was dissolved in chloroform and washed with saturated aqueous sodium carbonate and dried over magnesium sulphate. The resulting solution was evaporated to dryness in tacuo to give the title compound (0.18 g) (57%); $^1$H NMR (CDCl$_3$) inter alia 0.71 (3H, 1d, J 6.6 Hz), 0.78 (3H, t, J 7.5 Hz), 0.94 (3H, d, J 7 Hz), 0.96 (3H, s), 1.43 (3H, s), 1.7 (6H, t, J 7 Hz), 2.40 (1H, m), 2.94 (6H, t, J 7.5 Hz), 3.19 (2H, s), 3.41 (1H, d, J 8.4 Hz), 5.60 (1H, d). MS (EI) m/z 506 ($M^+$).

EXAMPLE 4

Mutilin 14-(quinuclidin-3-yloxy)-acetate hydrochloride

3-Quinuclidinol (0.635 g) in dry DMF (4 ml) was stirred under argon and treated with sodium hydride (0.21 g of a 60% dispersion in oil). After 1 hour the mixture was cooled to −15° C. and a solution of mutilin 14-methanesulfonyloxyacetate (2.28 g, see H. Egger and H. Reinshagen, J. Antibiotics 29 (9), 915) in dry DMF (4 ml) was added dropwise. The mixture was allowed to warm gradually to room temperature, left 1 hour and diluted with water (30 ml) and chloroform (30 ml). The layers were shaken and separated, the organic phase washed twice more with water, dried over MgSO$_4$ and evaporated. The residue was chromatographed on silica, eluting with dichloromethane/methanol/35% ammonia solution (19:1:0.1) to isolate a compound at $R_f$ approx. 0.45 on silica tlc, eluting with the same solvent mixture. A solution of this compound in chloroform (5 ml) was treated with 1N HCl in ether (2 ml) and evaporated to provide the title compound as a buff foam (0.339 g); $^v$max (CHCl$_3$) 3562, 3435 (broad), 2447 (broad), 1735 cm$^{-1}$; $^1$H NMR (CDCl$_3$) inter alia 0.71 (3H, d, J 6.7 Hz), 0.90 (3H, d, J 6.7 Hz), 3.1–3.6 (7H, m), 3.8–4.1 3H, m), 5.22 (1H, d, 17.5 Hz), 5.38 (1H, d, J 10.8 Hz), 5.81 (1H, d, J 8.3 Hz), 6.48 (1H, dd, J 14.7 and 11.0 Hz), 12.3 (1H, broad s, disappears on D$_2$O exchange); MS (+ve ion electrospray) m/z 488 (MH$^+$, 90%). 186 (100%).

EXAMPLE 5

Mutilin 14-(quinuclidin-3-ylsulfanyl)-acetate

The preparation of quinuclidin-3-thiol was based on patent literature (J. Barriere. C. Cotret and J. Paris, E.P. 248703 [1987]). A solution of triphenylphosphine (12 g) in THF (85 ml) was ice-cooled under argon and treated dropwise with diisopropyl azodicarboxylate (9 ml). After 30 minutes a solution of 3-quinuclidinol (2.9 g) and thiolacetic acid (3.24 ml) in THF (170 ml) was added dropwise over 1 hour. The mixture was stirred overnight at room temperature, evaporated and the residue taken up in ether (250 ml). This solution was extracted with 1M hydrochloric acid (2×40 ml), the combined aqueous extracts washed with ether (100 ml) and evaporated to dryness. The residue was desiccated under vacuum over P$_2$O$_5$ for 4 days to provide a pale yellow solid. A portion of this solid (0.443 g) was dissolved in ethanol (10 ml) and treated with sodium methoxide (0.216 g). After 1 hour, mutilin 14-methanesulfonyloxyacetate (0.912 g) was added, the mixture stirred a further 1 hour, diluted with chloroform (30 ml) and water (30 ml), shaken and separated. The organic layer was washed with water (30 ml), dried over MgSO$_4$ and evaporated. Chromatography of the residue on silica eluting with chloroform/methanol/35% ammonia solution (19:1:0.1) provided the title compound as a pale yellow foam, 0.62 g (62%); $^v$max (CHCl$_3$) 3563, 1730 cm$^{-1}$; $^1$H NMR (CDCl$_3$) inter alia 0.74 (3H, d, J 6 Hz), 0.88 (3H, d, J 7 Hz), 5.1–5.4 (2H, m), 5.76 and 5.77 (1H, 2d, J 8.3 Hz), 6.49 (1H, dd, J 17 and 11 Hz); MS (+ve ion electrospray) m/z 504 (MH$^+$, 100%), 202 (55%).

EXAMPLE 6

Mutilin 14-(quinuclidin-4-yl-sulfanyl)-acetate
Step 1. Quinuclidin-4-thiol hydrochloride Crude quinclidin-4-thiol hydrolodide (Eckharat et al., Helv. Chem. Acta, 57 (4), (1974) 2339–2345 (15.1 g, 0.057 mole) was dissolved in water (200 ml). Sodium carbonate (21.0 g, 0.2 mole) was added. The mixture was extracted with chloroform (200 ml×7). The combined organic extract was dried over MgSO$_4$ and concentrated in vacuo. To the concentrate was added 1M hydrogen chloride in ether (100 ml). The mixture was evaporated to dryness in vacuo to yield the title compound as a white solid 7.135 go (71%): $^1$H NMR (D$_2$O) 2.18 (6H, t, J 8 Hz), 3.40 (6H, t, J 8 Hz), MS (EI) m/z 144 ([(M-HCl)H]$^+$, 100%).
Step 2 Mutilin 14-(quinuclidin-4-yl-sulfanyl)-acetate Quinuclidin-4-thiol hydrochloride (5 g) was stirred with ethanol (110 ml) under argon and solid sodium methoxide (3.15 g) added. After 30 minutes mutilin 14-methanesulfonyloxyacetate (12.7 g) was added, followed by ethanol (30 ml). After a further 30 minutes the mixture was diluted with chloroform (250 ml) and water (250 ml), shaken and separated. The organic layer was washed with water (200 ml), dried over MgSO$_4$ and evaporated. Chromatography of the residue on silica, eluting with chloroform/methanol/35% ammonia solution (19:1:0.1) provided the title compound as a pale coloured foam (12.24 g), identical by NMR with the product of Example 1.

EXAMPLE 7

Mutilin 14-[N-(2,2-dimethylazabicyclo[4.3.0]non-4-ylmethyl)]-aminoacetate
Step 1 (±) Equatorial 4-cyano-2,2-dimethylazabicyclo [4.3.0]nonane To a mixture of (±) 2,2-dimethylazabicyclo[4.3.0]non-4-one (4.7 g, 0.028 mole), (F. D. King, J. Chem. Soc. Perkins. Trans 1, 447, 1986) and tosylmethylisocyanide (6.47 g, 0.033 mole) in dry dimethoxyethane (100 ml) at −10° C. was added ethanol (3.4 ml) followed by potassium-tert-butoxide (7.21 g, 0.064 mole). The mixture was stirred at −10° C. for 1 hour then warmed to 50° C. for 2 hours. The mixture was allowed to cool and diethyl ether (500 ml) added. Filtration and concentration of the filtrate in vacuo gave an oil. Column chromatography on silica gel elutin with ethyl acetate gave the title compound as an oil 3.0 g (60%); $^1$H NMR (CDCl$_3$) 0.95 (3H, s), 1.21 (3H, s), 1.35–1.51 (2H, m), 1.61–1.91 (4H, m), 2.15–2.19 (1H, m), 2.28–2.39 (2H, m), 2.57–2.71 (1H, m), 2.89–2.98 (1H, m).
Step 2 (±) Equatorial aminomethyl-2,2-dimethylazabicyclo [4.3.0]nonane (±) Equatorial 4-cyano-2,2- dimethylazabicyclo [4.3.0]nonane (1.0 g, 0.0056 mole) in tetrahydrofuran (50 ml) was treated with lithium aluminium hydride (1.07 g, 0.028 mole) and stirred at ambient temperature for 18 hours. Diethyl ether (50 ml) was then added followed by a mixture of water (4 ml) and 10% aqueous sodium hydroxide solution (1.5 ml). Filtration and concentration of the filtrate in vavuo gave the title compound 0.97, (95%) as an oil; $^1$H NMR (CDCl$_3$) 0.95 (3H, s), 1.20 (3H, s), 1.25–1.95 (9H, m), 2.25–2.40 (2H, m), 2.55 (2H, d, J 6 Hz), 2.89–2.97 (1H, m).

Step 3 Mutilin 14-[N-(2,2-Dimethylazabicyclo[4.3.0]non-4-ylmethyl)]-aminoacetate (±) Equatorial aminomethyl-2,2-dimethylazabicyclo[4.3.0]nonane (0.1 g, 0.0006 mole) was treated with mutilin 14-toluenesulfonyloxyacetate (0.25 g, 0.0005 mole), (K Riedl, J Antibiotics 29 (2), 133, 1976) and N,N-diisopropylethylamine (0.1 ml, 0.0006 mole) in ethanol (20 ml) and heated under reflux for 6 hours. The mixture was then concentrated in vacuo and the residue partitioned between saturated sodium hydrogen carbonate solution and dichloromethane. The organics were separated and dried (Na$_2$SO$_4$). Chromatography on silica gel eluting with chlorofom/methanol/35% ammonia solution (90:9:1) gave the title compound 0.08 g, (31%); $^1$H NMR (CDCl$_3$) 0.71 (3H, d, J 6.5 Hz) 0.90 (3H, d, J 6.5 Hz), 0.95 (3H, s), 1.25–2.55 (38H, m), 2.85–2.97 (1H, m), 3.19–3.39 (2H, m), 5.15 (1H, d, J 16.5 Hz), 5.31 (1H, d, J 11.1 Hz), 5.78 (1H, d, J 8.6 Hz), 6.50 (1H, dd, J 15.0 and 11.1 Hz). MS (+ve ion electrospray) m/z 543 (MH$^+$, 100%).

EXAMPLE 8

Mutilin 14-(quinuclidin-4-ylcarbonylamino)-acetate
Step 1. Mutilin 14-azidoacetate To a stirred solution of mutilin 14-toluenesulfonyloxyacetate (5.33 g, 0.01 mole) in acetone (50 ml) was added a solution of sodium azide (0.7 g 0.011 mole) in water (6.5 ml). A solid precipitated briefly then redissolved. The homogenous mixture was stirred for 2 hours at ambient temperature then heated to reflux for 3 hours. The mixture was concentrated in vacuo to low volume then diluted with chloroform. The resulting solution was washed three times with water then dried over magnesium sulfate. Concentration in vacuo gave a pale yellow foam which was purified by chromatography on silica gel. Elution with ethyl acetate/hexane mixtures provided the title compound as a white foam 3.3 g (82%); $^1$H NMR (CDCl$_3$) inter alia 0.73 (3H, d, J 6.8 Hz), 0.89 (3H, d, J 7.1 Hz), 1.23 (3H, s), 1.47 (3H, s), 3.37 (1H, dd, J 10.7 and 6.6 Hz), 3.77 (2H, s), 5.22 (1H, dd, J 17.4 and 1.3 Hz), 5.38 (1H, dd, J 11 and 1.3 Hz), 5.86 (1H, d, J 8.5 Hz), 6.49 (1H, dd, J 17.4 and 11 Hz).

Step 2. Mutilin 14-(triphenylphosphinimino)-acetate

Triphenylphosphine (0.275 g, 0.00105 mole) was added to a stirred solution of mutilin 14-azidoacetate (0.404 g, 0.001 mole) in dichloromethane maintained under an atmosphere of argon. The solution rapidly became homogenous and a gas was evolved. Stirring was continued for 17 hours; the mixture was then concentrated in vacuo to give the title compound as a white solid, obtained by filtration after trituration in petroleum ether 0.638 g (100%); MS (+ve ion electrospray) m/z 638 (MH$^+$, 100%)

Step 3. Mutilin 14-aminoacetate

Mutilin 14-(triphenylphosphinimino)-acetate (1 g, 0.00157 mole) was suspended in ethanol (25 ml) and potassium hydroxide (0.175 g, 0.00314 mole) was added. The mixture was stirred for 17 hours during which time it became homogeneous. 2M hydrochloric acid (1.7 ml) was then added, stirring continued for ten minutes and the mixture concentrated in vacuo. The residue was taken up in 2M hydrochloric acid and the solution washed three times with dichloromethane. The aqueous phase was then layered with dichloromethane and the pH adjusted to 11 by addition of solid potassium carbonate with vigorous stirring The organic phase was then separated, the aqueous phase extracted with dichloromethane, the combined organic extract washed with brine, dried over magnesium sulfate and concentrated in vacuo. The title compound was obtained as a white foam 0.505 g (85%); $^1$H NMR (CDCl$_3$) inter alia 0.71 (3H, d, J 6.5 Hz), 0.89 (3H, d, J 6.9 Hz), 1.17 (3H, s), 1.45 (3H, s), 3.33 (3H, m), 5.21 (1H, d, J 17.4 Hz), 5.36 (1d, J 11 Hz), 5.78 (1H, d, J 8.4 Hz), 6.52 (1H, dd, J 17.4 and 11 Hz).

Step 4. Quinuclidin-4-ylcarbonyl chloride hydrochloride

Quinuclidine-4-carboxylic acid hydrochloride (0.192 g, 0.001 mole) was suspended in dichloromethane (5 ml) and dimethylformamide (1 drop) and oxalyl chloride (0.436 ml. 0.635 g, 0.005 mole) were added. The resulting suspension was heated to reflux under an atmosphere of argon for six hours. Following concentration of the suspension in vacuo the residue was suspended in dichloromethane, concentrated in vacuo and finally dried in vacuo to give the title compound as a pale brown solid.

Step 5. Mutilin 14-(quinuclidin-4-ylcarbonylamino)-acetate

Quinuclidin-4-ylcarbonyl chloride hydrochloride (0.001 mole theoretical, Step 4) was suspended in dichloromethane (6 ml) and mutilin 14-aminoacetate (0.126 g, 0.00033 mole) was added. To the stirred suspension, under an atmosphere of argon, was added triethylamine (0.278 ml. 0.202 g 0.002 mole) and stirring continued for 18 hours. Chloroform and water were added and the pH of the aqueous phase adjusted to 11 by addition of solid potassium carbonate. After shaking, the phases were separated, the organic phase was washed once with saturated aqueous sodium hydrogen carbonate and once with brine, dried over magnesium sulfate and concentrated in vacuo to give the crude product as an off-white foam. Purification by chromatography on silica gel eluting with chloroforn/methanol/35% ammonia solution provided a pale yellow glass. The product was dissolved in 2M hydrochloric acid, the solution washed twice with dichloromethane, then layered with dichloromethane. The pH of the aqueous phase was adjusted to 11 by addition of solid potassium carbonate. After shaking, the organic phase was separated, dried over magnesium sulfate and concentrated in vacuo. The residue was repeatedly dissolved in chloroform and concentrated in vacuo. Finally the residue was triturated with diethyl ether to give the title compound as a buff solid 0.0019 (11%); $^1$H NMR (CDCl$_3$) inter alia 0.71 (3H, d, J 6.9 Hz), 0.88 (3H, d, J 7 Hz), 1.18 (3H, s), 1.45 (3H, s), 2.96 (6H, m), 3.37 (1H, m), 3.93 (2H, d, J 4.9 Hz), 5.23 (1H, d, J 17.4 Hz), 5.36 (1H, d, J 11 Hz), 5.79 (1H, d, J 8.5 Hz), 6.02 (1H, m(br)), 6.47 (1H, dd, J 17.4 and 11 Hz); MS (+ve ion electrospray) m/z 515 (MH$^+$, 100%).

EXAMPLE 9

Mutilin 14-[(3R,4R)-Azabicyclo[2.2.1]hept-3ylcarbonylamino]-acetate
Step 1. (3R,4R)-Azabicyclo[2.2.1]hept-3-ylcarbonyl chloride hydrochloride 3R,4R-Azabicyclo[2.2.1]heptane-3-carboxylic acid hydrobromide (0.127 g 0.0005 mole) was suspended in dichloromethane (2 ml) and dimethylformamide (1 drop) and oxalyl chloride (0.131 ml, 0.191 g, 0.0015 mole) were added. The mixture was stirred for 4 hours under an atmosphere of argon. The resulting homogenous solution was concentrated in vacuo, the residue was dissolved in dichloromethane, concentrated in vacuo and finally dried in vacuo to give the title compound as an off-white solid.

Step 2. Mutilin 14-[(3R,4R)-Azabicyclo[2.2.1]hept-3ylcarbonylamino]-acetate (3R.4R)-Azabicyclo[2.2.1]hept-3-ylcarbonyl chloride hydrochloride (0.0005 mole theoretical, Step 1) was dissolved in dichloromethane (4 ml) and mutilin 14-aminoacetate (0.126 g, 0.00033 mole) was added. To the stirred solution under an atmosphere of argon was added triethylamine (0.134 ml. 0.101 g, 0.001 mole). The resulting solution was stirred for 17 hours. Chloroform and water were added and the pH of the aqueous phase adjusted to 11 by addition of solid potassium carbonate. After shaking, the phases were separated, the organic phase was washed once with saturated aqueous sodium hydrogen carbonate and once with brine, dried over magnesium sulfate and concentrated in vacuo to give the crude product as an off-white foam. Purification by chromatography on silica gel eluting with chloroformn/methanol/35% ammonia solution provided the product as a white foam 0.142 a (86%); $^1$H NMR (CDCl$_3$) inter alia 0.72 (3H, d, J 6.9 Hz), 0.89 (3H, d, J 7 Hz), 1.18 (3H, s), 1.46 (3H, s), 3.37 (1H, m(br)), 3.96 (2H, d, J 5.1 Hz), 5.22 (1H d, J 17.4 Hz), 5.36 (1H, d, J 11 Hz), 5.78 (1H, d, 8.4 Hz), 5.96 (1H, m(br)), 6.47 (1H, dd, J 17.4 and 11 Hz),; MS (+ve ion electrospray) m/z 501 (MH$^+$, 40%).

EXAMPLE 10

Mutilin 14-(1-methylpiperid-4-ylcarbonylamino)-acetate

Step 1.1-Methylpiperid-4-ylcarbonyl chloride hydrochloride

1-Methylpiperidine-4-carboxylic acid hydrochloride (0.09 g, 0.0005 mole) was suspended in dichloromethane (5 ml) and dimethylformamide (1 drop) and oxalyl chloride (0.131 ml, 0.19 g, 0.0015 mole) were added. The mixture was stirred for 4 hours under an atmosphere of argon. The resulting homogenous solution was concentrated in vacuo, the residue was dissolved in dichloromethane, concentrated in vacuo and finally dried in vacuo to give the title compound as an off-white solid.

Step 2. Mutilin 14-(1-methylpiperid-4-ylcarbonylamino)-acetate

1-Methylpiperid-4-ylcarbonyl chloride hydrochloride (0.0005 mole theoretical, Step 1) was dissolved in dichloromethane (4 ml) and mutilin 14-aminoacetate (0.126 g, 0.00033 mole) was added. Triethylamine (0.139 ml, 0.101 g, 0.001 mole) was added to the stirred solution under an atmosphere of argon. After 2 hours chloroform and water were added and the pH of the aqueous phase adjusted to 11 by addition of solid potassium carbonate. After shaking, the phases were separated, the organic phase was washed once with saturated aqueous sodium hydrogen carbonate and once with brine, dried over magnesium sulfate and concentrated in vacuo to give the crude product as an off-white foam. Purification by chromatography on silica gel eluting with chloroform/methanol/35% ammonia solution provided the product as a white foam 0.150 g (90%); $^1$H NMR (CDCl$_3$) inter alia 0.71 (3H, d, J 6.8 Hz), 0.89 (3H, d, J 7 Hz), 1.18 (3H, s), 1.45 (3H, s), 3.36 (1H, m), 3.94 (2H, d, J 5 Hz), 5.9 (1H, d, J 18.6 Hz), 5.35 (1H, d, J 12.2 Hz), 5.78 (1H, d, J8.4 Hz), 5.99 (1H, m(br)), 6.47 (1H, dd, J 17.4 and 11 Hz); MS (+ve ion electrospray) m/z 503 (MH$^+$, 25%).

EXAMPLE 11

Mutilin 14-[3-(1-methylpiperid-4-yl)]-propionate
Step 1. 3-(1-Methylpiperid-4-yl)propionyl chloride A suspension of 3-(1-methylpiperid-4-yl)propionic acid hydrochloride (WO 9620173 A1, Example 1)(0.33 g, 0.00159 mole) in dry dichloromethane (10 ml) was treated with dimethylformamide (1 drop) and oxalyl chloride (0.416 ml, 0.605 g, 0.00477 mole) under an atmosphere of argon. After stirring for 3½ hours the mixture was concentrated in vacuo. The residue was dissolved in dry dichloromethane and concentrated in vacuo to give the title compound as a white solid.

Step 2.

A solution of 3-(1-methylpiperid-4-yl)propionyl chloride (0.00159 mole theoretical, Step 1) and (3R)-3-deoxo-11-deoxy -3-methoxy -11-oxo-4-epi-mutilin (H Berner. G. Schulz and H. Schneider, *Tetrahedron*, 1980, 36, 1807) in dry dimethylformamide was heated at 110° C. under argon for 17 hours. The mixture was then concentrated in vacuo and the residue chromatographed on silica gel eluting with dichloromethane/methanol/35% ammonia solution mixtures. The title compound was obtained as a pale yellow oil 0.284g, (49%); $^1$H NMR (CDCl$_3$) inter alia 0.79 (3H, d, J 6.9 Hz), 0.99 (3H, d, J 6.4 Hz), 1.18 (3H, s), 1.24 (3H, s), 2.37 (3H, s), 2.97 (3H, m), 3.23 (3H, s), 3.48 (1H, m), 5.01 (1H, d, J 17.6 Hz), 5.30 (1H, d, J 10.7 Hz), 5.74 (1H, d, J 10 Hz), 6.67 (1H, dd, J 17.5 and 10.6 Hz); MS (+ve ion electrospray) m/z 488 (MH$_3$, 100%).

Step 3. Mutilin 14-[3-(1-methylpiperid-4-yl)]-propionate

A solution of (3R)-3-deoxo-11-deoxy-3-methoxy-11-oxo-4-epi-mutilin (0.355 g, 0.000728 mole) in dioxan (3 ml) was treated with concentrated hydrochloric acid (3 ml). After 4 hours the mixture was diluted with water, layered with dichloromethane and the vigorously stirred mixture adjusted to pH 11 by addition of solid potassium carbonate. The phases were then separated and the aqueous phase extracted with dichloromethane. The combined organic extract was washed with saturated aqueous sodium hydrogen carbonate and brine, dried over magnesium sulfate and concentrated in vacuo. The residue was chromatographed on silica el eluting with dichloromethane/methanol/35% ammonia solution (90:9: 1) to give the title compound as a white foam 0.284 g (82%); $^1$H NMR (CDCl$_3$) inter alia 0.70 (3H, d, J 6.6 Hz), 0.88 (3H, d, J 7 Hz), 1.17 (3H, s), 1.45 (3H, s), 2.44 (3H, s), 3.05 (2H, m), 3.36 (1H, dd, J 11.4 and 7.4 Hz), 5.20 (1H, d, J 17.5 Hz), 5.36 (1H, d, J 11 Hz), 5.74 (1H, d, J 8.4 Hz), 6.51 (1H, dd, J 17.5 and 11 Hz); MS (+ve ion electrospray) m/z 474 (MH$^+$, 100%).

EXAMPLE 12

Mutilin 14-(quinuclid-4-ylmethylsulfanyl)-acetate

An ice cooled solution of triphenylphosphine (1.19 g, 0.0042 mole) in dry tetrahydrofuran was treated dropwise with diisopropyl azodicarboxylate (0.85 g, 0.0042 mole). After 30 minutes a solution of quinuclid-4-ylmethanol (0.565 g, 0.004 mole) and thiolacetic acid (0.315 ml, 0.0042 mole) in dry tetrahydrofuran (20 ml) added dropwise over a period of 10 minutes. The mixture was left at 5° for 72 hours then concentrated in vacuo and the residue dissolved in ether (200 ml). The resulting solution was extracted with 1M hydrochloric acid (3×50 ml). The combined extract was concentrated in vacuo and dried in vacuo to give a gummy residue 0.65 g. The residue was dissolved in ethanol (30 ml) and treated under argon with potassium tert butoxide (0.785 g, 0.007 mole) for 30 minutes. Mutilin 14-methanesulfonyloxyacetate 1.38 g. 0.003 mole) was then added to the ethanolic solution and the mixture stirred overnight under argon. The insoluble byproducts were filtered off and the filtrate evaporated to dryness. The residue was partitioned between chloroform and water. The organic layer washed with brine and dried over magnesium sulfate and evaporated to dryness. Chromatography of the residue on silica gel eluting with chloroform/methanol/35% ammonia solution (19:1:0.1) provided the title compound as a white foam, 0.48 g (31%); $^1$H NMR (CDCl$_3$) inter alia 0.74 (3H, d, J 6.6 Hz), 0.88 (3H, d, J 7 Hz), 1.76 (3H, s), 1.44 (6H, t, J 7.7 Hz), 2.47 (2H, s), 2.87 (6H, t, J 7.5 Hz), 3.09 (2H, s), 3.36 (1H, m), 5.1–5.4 (2H, m), 5.75 (1H, d, J 8.3 Hz), 6.48 (1H, m); MS (+ve ion electrospray) m/z 518 (MH$^+$, 100%).

EXAMPLE 13

19,20-Dihydromutilin 14-(quinuclidin-4-ylsulfonyl)acetate 19,20-Dihydromutilin 14-(quinuclidin-4-ylthio)acetate (0.05 g, 0.0001 mole) in dry tetrahydrofuran (2 ml) and tert-butanol (0.2 ml) was treated with N-methylmorpholine oxide (0.036 g. 0.003 mole) and a catalytic amount of osmium tetroxide under argon for a period of 4.5 hours. The mixture was extracted with ethyl acetate. The organic solution was filtered to remove inorganic residues. The filtrate was concentrated in vacuo. Chromatography of the residue on silica gel eluting with chloroform/methanol/35% ammonia solution provided the title compound as a foam, 0.043 g (80%); $^1$H NMR (CDCl$_3$) inter alia 0.70 (3H, d, J 7 Hz), 0.82 (3H, t, J 7 Hz), 0.93 (3H, d, J 7 Hz), 0.96 (3H, s), 1.92 (6H, t, J 7.5 Hz), 3.01 (6H, t, J 7.5 Hz), 3.41 (1H, m), 3.73 (1H, d, J 13.3 Hz), 3.87 (1H, d, J 13.3 Hz), 5.68 (1H, d, J 8 Hz); MS (+ve ion electrospray) m/z 538 (MH$^+$, 60%).

EXAMPLE 14

19.20-Dihydromutilin 14-(quinclidin-4-ylsulfoxy)-acetate

A cooled solution of 19,20-dihydromutilin 14-(quinuclidin-4-ylthio)-acetate (0.152 g, 0.0003 mole) and glacial acetic acid (0.06 g, 0.001 mole) in chloroform (5 ml) was treated with 80% 3-chloroperoxybenzoic acid (0.069 g, 0.0032 mole) at 0° C., allowed to warm to room temperature and stirred for 72 hours. The solvents were removed in vacuo. Chromatography of the residue on silica gel eluting with chloforn/methanol/35% ammonia solution (20:1:0.1) provided the title compound as a white solid, 0.064 g (41%); $^1$H NMR (CDCl$_3$) inter alia 0.72–0.95 (12H, m), 1.45 (6H, t, J 8.5 Hz), 1.74 (6H, t, J 8 Hz), 2.13–2.25 (3H, m), 2.39 (1H, m), 3.02 (6H, t, J 7.6 Hz), 3.35–3.42 (3H, m), 5.71 (1H, d, J 8.4 Hz); MS (+ve ion electrospray) m/z 522 (MH$^+$, 100%).

EXAMPLE 15

Mutilin-14-(1-methylpiperid-4-ylsulfanyl)-acetate

A solution of triphenylphosphine (5.51 g, 0.021 mole) in dry tetrahydrofuran (100 ml) was ice-cooled under argon and treated with diIsopropyl azodicarboxylate (4.25 g, 0.021 mole). After 30 minutes a solution of 4-hydroxy-1-methylpiperidine (2.3 g, 0.02 mole) and thiolacetic acid (1.54 g, 0.02 mole) in dry tetrahydrofuran (50 ml) was added over a period of 30 minutes. The mixture was stirred overnight at room temperature, evaporated in vacuo and the residue taken up in ether (200 ml). The ethereal solution was extracted with 1M hydrochloric acid (50 ml×4). The combined aqueous extract was washed with ether, evaporated to drvness and dried in vacuo to give a yellow gum (2.4 g). A portion of this gum (0.517 g) was dissolved in ethanol and treated with potassium tert-butoxide (0.785 g) under argon for 30 minutes. Mutilin-14-methanesulfonyloxyacetate (0.92 g, 0.002 mole) was added and the mixture stirred overnight, then concentrated in vacuo. The residue was partitioned between chloroform and water. The organic layer was washed with brine, dried over magnesium sulfate and concentrated in vacuo. Chromatography on silica gel eluting with chloroform/methanol/35% ammonia solution provided the title compound as a foam, 0.557 g (57%); $^1$H NMR (CDCl$_3$) inter alia 0.73 (3H, d, J 6.5 Hz), 0.87 (3H, d, J 7 Hz), 1.30 (3H, s), 1.67 (3H, s), 2.25 (3H, s), 3.16 (2H, s), 3.36 (1H, m), 5.28 (2H, m), 5.77 (1H, d, J 8.5 Hz), 6.47 (1H, m); MS (+ve ion electrospray) m/z 492 (MH$^+$, 100%).

EXAMPLE 16

Mutilin 14-{(3RS,4SR)-1-aza-bicyclo[2.2.1hept-3-yl-sulfanyl}-acetate

The title compound was prepared in 32% overall yield from endo-3-hydroxyazabicyclo[2.2.1 heptane (S. M. Jenkins et al, *J. Med. Chem.*; 1992, 35, 2392–2406) using the procedure described in Example 5. The title compound was isolated as a colourless solid, in the $^1$H NMR spectrum the 8 line multiplets at d 3.05–3.40 and 6.43–6.56 indicate a 1:1 mixture of diastereoisomers; $^1$H NMR (CDCl$_3$) inter alia 0.74 (3H, d, J 6.4 Hz), 0.88 (3H, d, J 7.0 Hz), 3.05–3.40 (2H, m), 5.21 (1H, d, J 17.5 Hz), 5.35 (1H, d, J 11.0 Hz), 5.75–5.80 (1H, m), 6.43–6.56 (1H, m); MS (+ve electrospray) m/z 490 (MH$^+$).

EXAMPLE 17

Mutilin 14-{(3RS,4SR)-1-aza-bicyclo[2.2.1]hept-3-yl-sulfanyl}-acetate hydrochloride The title compound was prepared from mutilin 14-{(3RS, 4SR)-1-azabicyclo(2.2.1]hept-3-yl-sulfanyl }-acetate using the procedure described in Example 2. The title compound was isolated as a colourless solid, 1:1 mixture of diastereoisomers; $^1$H NMR (DMSO-d$_6$) inter alia 0.65 (3H, d, J 6.4 Hz), 0.84 (3H, d, J 6.8 Hz), 1.09 (3H, s), 1.39 (1H, s), 4.61 (1H, d, J 5.2 Hz, exchanged with D$_2$O), 5.05–5.12 (2H, m), 5.60 (1H, d, J 7.9 Hz), 6.14 (1H, dd, J 18 and 10.7 Hz), 10.4–10.6 (1H, br, exchanged with D$_2$0); MS (+ve electrospray) m/z 490 (MH$^+$ of free base).

EXAMPLE 18

Mutilin 14-(quinuclidin-3-ylidene)-acetate hydrochloride (both Geometric isomers)

Step 1. Methyl quinuclidin-3-ylidene acetate hydrochloride

A suspension of quinuclidin-3-one hydrochloride (3.23 g) in DMF (20 ml) was treated with sodium methoxide (1.08 g) and stirred vigorously for 30 minutes. A solution of trimethyl phosphonoacetate (4.05 ml) and sodium methoxide (1.35 g) in DMF (20 ml) was added dropwise over 15 minutes and stirred a further 2½ hours. The DMF was evaporated and the residue treated with dry ether (100 ml), triturated and filtered. The filtrate was treated with 1N HCl in ether (30 ml), the resulting solid triturated and the ether decanted. Ether (200 ml) was added, the suspension stirred vigorously for 30 minutes, the solid filtered off and heated at 60° C. under vacuum for 2 days. The resulting methylquinuclidin- 3-ylideneacetate hydrochloride (3.93 g) was a ca. 1:1 mixture of geometric isomers; $^1$H NMR (D$_2$O) inter alia 5.84 (broad s) and 5.94 (t, J 2.5 Hz) (vinyl protons of the two geom. isomers).

Step 2. Quinuclidin-3-ylideneacetic acid hydrochloride

Methyl quinuclidin-3-ylideneacetate hydrochloride (1 g) was heated in concentrated hydrochloric acid (10 ml) at 60° C. for 18 hrs and the solution evaporated to dryness. The residue was kept under vacuum over P$_2$O$_5$ for 3 days to give quinuclidin-3-ylidene acetic acid hydrochloride, 0.91 g (97%) as a white solid; $^1$H NMR (D$_2$O) inter alia 5.77 (broad s) and 5.86 (broad s) (ca. 1:1, vinyl protons of the two geom. isomers).

Step 3. (3R)-3-deoxo-11-deoxy-3-methoxy-11-oxo-4-epimutilin 14-(quinuclidin-3-ylidene)-acetate Quinuclidin-3-ylideneacetic acid hydrochloride (0.204 g) was suspended in chloroform (5 ml), stirred under argon and treated with 1 drop DMF and oxalyl chloride (0.87 ml). After 2 hours the solvent was evaporated, toluene (10 ml) added to the residue and evaporated. The residue was taken up in DMF (2 ml), treated with (3R)-3-deoxo-11-deoxy-3-methoxy-11-oxo-4-epimutilin (0.334 g, prepared according to H. Berner, G. Schulz and H. Schneider, *Tetrahedron* (1980) 36, 1807) and heated at 100° C. under argon for 3 hours. After leaving at room temperature overnight, the mixture was diluted with chloroform (20 ml), washed with aqueous NaHCO$_3$ and water, dried and evaporated to dryness. Chromatography on silica. eluting with chloroform/methanol/35% ammonia solution (19:1:0.1) separated the 2 geometric isomers of the title compound.

Less polar isomer, 0.1 g (20%); $^1$H NMR (CDCl$_3$) inter alia 3.23 (3H, s), 3.4–3.6 (1H, m), 3.96 (2H, ABq, J 20 Hz), 5.02 (1H, d, J 17.5 Hz), 5.34 (1H, d, J 10.5 Hz), 5.64 (1H, t, J 2.5 Hz), 5.81 (1H, d, J 10 Hz), 6.74 (1H, dd, J 17.5 and 10.5 Hz); MS (+ve ion electrospray) m/z 484 (MH$^+$, 100%).

More polar isomer, 0.234 g (48%); $^1$H NMR (CDCl$_3$) inter alia 3.12 (2H, s), 3.23 (3H, s), 3.4–3.5 (1H, m), 5.01 (1H, d, J 17.5 Hz), 5.30 (1H, d, J 10.5 Hz), 5.78 (1H, d, J 10 Hz), 6.37 (1H, d, J 0.95 Hz), 6.65 (1H, dd, J 17.5 and 10.5 Hz); MS (+ve ion electrospray) m/z 484 (MH$^+$, 100%).

Step 4. Mutilin 14-(quinuclidin-3-ylidene)-acetate hydrochloride

The less polar geometric isomer of (3R)-3-deoxo-11-deoxy-3-methoxy-11-oxo-4-epimutilin 14-(quinuclidin-3-ylidene)-acetate (0.1) was dissolved in dioxan (3 ml), briefly cooled in ice-water and treated with conc. HCl (2 ml). After 5 hours at room temperature CHCl$_3$ (10 ml) and water (20 ml) were added, followed by solid NaHCO$_3$ until basic. The layers were separated, the aqueous re-extracted with CHCl$_3$ and the combined organic dried and evaporated. The residue was chromatographed, eluting with chloroform/methanol/35% ammonia solution 97:3:0.3 and the product in chloroform solution treated with 1M HCl in ether (1 ml). Evaporation gave the less polar geometric isomer of the title compound as a white foam. 0.105 g; $^1$H NMR (CD$_3$SOCD,) inter alia 2.85 (1H, s), 4.38 (2H, ABq, J 19 Hz), 4.59 (1H, d, J 6 Hz, disappears on D$_2$O exchange), 5.0–5.2 (2H, m), 5.64 (1H, d, J 8 Hz), 5.92 (1H, s), 6.27 (1H, dd, J 17.5 and 11 Hz), 10.7 (1H, broad s, disappears on D$_2$O exchange); MS (+ve ion electrospray) m/z 470 (MH$^+$-HCl, 100%).

In the same manner, the more polar geometric isomer of (3R)-3-deoxo-11-deoxy-3-methoxy-11-oxo-4-epimutilin 14-(quinuclidin-3-ylidene)-acetate (0.116 g) was converted into the more polar geometric isomer of the title compound (0.096 g) as an off-white foam; 1H NMR (CD$_3$SOCD$_3$) inter alia 4.62 (1H, d, J 6 Hz, disappears on D$_2$O exchange), 5.0–5.2 (2H, m), 5.65 (1H, d, J 8 Hz), 6.18 (1H, dd, J 17.5 and 11 Hz), 6.64(11H, s), 11.42 (1H, broad s, disappears on D$_2$O exchange); MS (+ve ion electrospray) m/z 470 (MH$^+$-HCl, 100%).

EXAMPLE 19

Mutilin 14-[(±)-quinuclidin-3-yl]-acetate hydrochloride

Step 1. (±)-Quinuclidine-3-acetic acid hydrochloride

A mixture of methyl quinuclidin-3-ylideneacetate hydrochloride (Example 18, Step 1) (2 g), ethanol (50 ml), 2M hydrochloric acid (5 ml) and 10% Pd/C (1 g) was stirred for 24 hours under H$_2$ at atmospheric pressure, filtered through celite and evaporated to dryness. The residue was dissolved in concentrated hydrochloric acid (10 ml). heated at 60° C. for 18 hours, treated with a further 10 ml of concentrated hydrochloric acid, heated at 80° C. for 6 hours and evaporated to dryness. The residue was kept under vacuum over P$_2$O$_5$ for 3 days to give the title compound as a white solid (1.8 g); MS (+ve ion electrospray) m/z 170 (MH$^+$, 100%).

Step 2. (3R)-3-deoxo-11-deoxy-3-methoxy-11-oxo-4-epimutilin 14-[(±)-quinuclidin-3-yl]-acetate (±)-Quinuclidine-3-acetic acid hydrochloride was converted into acid chloride and reacted with (3R)-3-deoxo-11-deoxy-3-methoxy-11-oxo-4-epimutilin in the manner of Example 18, Step 3. Chromatography of the product gave the title compound as a white foam (68%); $^1$H NMR (CDCl$_3$) inter alia 3.23 (3H, s), 3), 3.3–3.5 (1H, m), 5.01 (1H, d, J 17.5 Hz), 5.32 (1d, J 10.5 Hz), 5.75 (1H, d, J 9.8 Hz), 6.68 and 6.69 (1H, 2 dd, J 17.5 and 10.5 Hz); MS (+ve ion electrospray) m/z 486 (MH$^+$, 100%).

Step 3. Mutilin 14-[(±)-quinuclidin-3-yl]-acetate hydrochloride

Rearrangement of (3R)-3-deoxo-11-deoxy-3-methoxy-11-oxo-4-epimutilin 14-[(±)-quinuclidin-3-yl]acetate in the manner of Example 18. Step 4 gave the title compound as a white foam (95%); $^1$H NMR (CDCl$_3$) inter alia 5.1–5.4 (2H, m), 5.74 (1H, d, J 8.3 Hz), 6.43 and 6.47 (1H, 2 dd, J 17.5 and 10.5 Hz); MS (+ve ion electrospray) m/z 472 (MH$^+$, 100%).

EXAMPLE 20

Mutilin 14-[(±)-quinuclidin-3-ylacetoxy]-acetate hydrochloride (±)-Quinuclidine-3-acetic acid hydrochloride (0.206 g) was suspended in chloroform (5 ml) under argon, treated with DMF (1 drop) and oxalyl chloride (0.87 ml) and stirred1 hour. The solution was evaporated, toluene was added and evaporated and the residue taken up in DMF (2 ml). Pleuromutilin (0.378 g) was added and the mixture stirred under argon for 18 hours, then heated at 110° C. for 30 minutes. It was diluted with chloroform (10 ml), washed with aqueous NaHCO$_3$ (twice) and water, dried and evaporated. The residue was chromatographed, eluting with chloroform/methanol/35% ammonia solution (9:1:0.1). A chloroform solution of the material obtained was treated with 1M HCl in ether (2 ml) and evaporated. Trituration under ether and filtration gave the title compound as an off-white solid, 0.22 g (42%); $^1$H NMR (CD$_3$SOCD$_3$) interalia 4.5–4.7 (3H, m, reduces to 2H, m on D$_2$O exchange); 5.0–5.2 (2H, m), 5.59 (1H, d, J 8 Hz), 6.10 (1H, dd, J 17.5 and 10.5 Hz), 10.06 (1H, broad s, disappears on D$_2$O exchange); MS (+ve ion electrospray) m/z 530 (MH$^+$, 100%).

EXAMPLE 21

Mutilin 14-(quinuclidin-3-ylmethylsulfanyl)-acetate

Step 1. Mixture of (±)-quinuclidin-3-ylmethylsulfanylacetate hydrochloride and (±)-quinuclidin-3ylmethanethiol hydrochloride (±)-Quinuclidine-3-methanol (L. I. Mastafonova, L. N Yakhontov, M. V. Rubtsov, Khim. Geterotsikl. Soedin., Akad. Nauk Latv. SSR. 1965(6), 858–863) was converted into the title mixture using the procedure of Example 5. MS (+ve ion electrospray) m/z 200 (MH$^+$ for thioacetate, 100%), 158 (MH$^+$ for thiol, 40%).

Step 2. Mutilin 14-(±)-quinuclidin-3-ylmethylsulfanyl)-acetate

The mixture from Step 1 was reacted with mutilin $^{14}$-methanesulfonyloxyacetate in the manner described in Example 5 to provide the title compound as an off-white foam (28%); $^1$H NMR (CDCl$_3$) inter alia 0.75 (3H, d, J 6.7 Hz), 0.89 (3H, d, J 7.0 Hz), 3.12 (2H, s), 3.37 (1H, broad, becomes d, J 6.3 Hz on D$_2$O exchange), 5.21 (1H, d, J 17.5 Hz), 5.36 (1H, d, J 11 Hz), 5.75 (1H, d, J 8.4 Hz), 6.51 (1H, dd, J 17.5 and 11 Hz); MS (positive ion electrospray) m/z 518 (MH$^+$, 100%).

EXAMPLE 22

1,2-Didehydromutilin 14-(quinuclidin-4-ylsulfanyl-acetate

Step 1. 1,2-Didehydromutilin-14-methanesulfonloxyacetate 1,2-Didehydropleuromutilin (0.2 g, 0.00053 mole) (G. Schulz and H. Berner. *Tetrahedron*, (1984) 40, 905–17) was converted to 1,2-didehydromutilin-14-methanesulfonyloxyacetate by the method previously described for pleuromutilin (H. Egger and H. Reinshagen. *J. Antibiotics* (1976), 29, 915–22) providing the product as a yellow foam, (100%); $^1$H NMR (CDCl$_3$) inter alia 0.80 (3H, d, J 6.7 Hz), 1.10 (3H, d, J 7.0 Hz), 1.16 (3H, s), 1.54 (3H, s), 3.21 (3H, s), 4.67 (2H, s), 5.22 (1H, dd, J 17.4 and 1.3 Hz), 5.38 (1H, dd, J 11 and 1.2 Hz), 5.81 (1H, d, J 8.9 Hz), 6.05 (1H, d, J 6.1 Hz), 6.44 (1H, dd, 17.3 and 11 Hz), 7.74 (1H, d, J 6.1 Hz).

Step 2. 1,2-Didehydromutilin 14-(quinuclidin-4-ylsulfanyl)-acetate

A solution of 1,2-didehydromutilin 14-methanesulfonyloxyacetate (0.00053 moles) in ethanol was treated with quinuclidin-4-thiol hydrochloride (0.105 g. 0.000583 mole). After 15 minutes sodium methoxide (0.057 g, 0.00106 mole) was added to the stirred solution. After 1 hour the mixture was concentrated in vacuo to a slurry. Chloroform and water were then added. The pH of the aqueous phase was adjusted to 11–12 by addition of solid potassium carbonate. The phases were separated and the aqueous re-extracted with chloroform. The combined organic extract was dried over magnesium sulfate and concentrated in vacuo. Purification by chromatography on silica gel eluting with chloroform/methanol/35% ammonia solution provided the product as an off-white foam 0.19 g (72%); $^1$H NMR (CDCl$_3$) inter alia 0.80 (3H, d, J 6.4 Hz), 1.08 (3H, d, J 7 Hz), 1.15 (3H, s), 1.55 (3H, s), 3.20 (2H, ABq), 5.20 (1H, dd, J 17.4 and 1.4 Hz), 5.35 (1H, dd, J11 and 1.4 Hz), 5.74 (1H, d, J8.7 Hz), 6.04 (1H, d, J6.1 Hz), 6.47 (1H, dd, J 17.3 and 11 Hz), 7.74 (1H, d, J 6.1 Hz); MS (−ve ion electrospray) m/z 500 ([M-H]$^-$, 50%).

EXAMPLE 23

2α-Hydroxymutilin 14-(quinuclidin-4-ylsulfanyl)-acetate

Step 1. 2-Diazomutilin 14-methanesulfonyloxyacetate

2-Diazopleuromutilin (0.809 g, 0.002 mole) (G. Schulz and H. Berner, *Tetrahedron* (9184), 40, 905–17) was converted to 2-diazomutilin-14-methanesulfonyloxyacetate by the method described for pleuromutilin (H. Egger and H. Reinshagen, *J. Antibiotics* (1976), 29, 915–22) providing the product as a bright yellow gum (100%); $^1$H NMR (CDCl$_3$) inter alia 0.75 (3H, d, J 6.9 Hz), 0.93 (3H, d, J 6.9 Hz), 1.18 (3H, s), 1.50 (3H, s), 3.20 (3H, s), 4.65 (2H, s), 5.24 (1H, d, J 17.5 Hz), 5.37 (1H, d, 11 Hz), 5.84 (1H, d, J8.5 Hz), 6.43 (1H, dd, J 17.4 and 11 Hz).

Step 2. 2α-Dichloroacetoxymutilin-14-methanesulfonyloxyacetate

2-Diazomutilin-14-methanesulfonyloxyacetate (0.002 moles theoretical) from Step 1 in dichloromethane (20 ml) was cooled in an ice bath under an atmosphere of argon. To the stirred solution was added dichloroacetic acid (0.309 g, 0.0024 mole), dropwise over 2 minutes. Stirring was continued for 2.5 hours. The mixture was diluted with dichloromethane and washed twice with saturated aqueous sodium hydrogen carbonate and once with brine. After drying over magnesium sulfate concentration in vacuo gave the product as a pale yellow foam (100%); $^1$H NMR (CDCl$_3$) inter alia 0.76 (3H, d, J 6 Hz), 0.93 (3H, d, J 7 Hz), 1.12 (3H, s), 1.49 (3H, s), 3.20 (3H, s), 4.66 (2H, s), 5.05 (1, t, J 9 Hz), 5.25 (1H, d, J 17.3 Hz), 5.38 (1H, d, J 11 Hz), 5.83 (1H, d, J 8.5 Hz), 5.97 (1H, s), 6.43 (1H, dd, J 17.4 and 11 Hz).

Step 3. 2α-Hydroxymutilin 14-(quinuclidin-4-ylsulfanyl)-acetate

2-Dichloroacetoxymutilin-14-methanesulfonyloxyacetate (0.001 mole theoretical) from Step 2 in ethanol (2 ml) was added to a pre-mixed solution of quinuclidine-4-thiol hydrochloride (0.27 g, 0.0015 mole) and sodium methoxide (0.162 g, 0.003 mole) in ethanol (8 ml). After stirring for 1 hour the mixture was diluted with chloroform, washed twice with saturated sodium hydrogen carbonate and once with brine, then dried over magnesium sulfate. Concentration in vacuo was followed by silica gel chromatography, eluting with chloroform/methanol/35% ammonia solution. The product was obtained as a white foam 0.2 g (38% overall, 3 steps); $^1$H NMR (CDCl$_3$) inter alia 0.75 (3H, d, J 6.5 Hz), 0.92 (3H, d, J 7 Hz), 1.17 (3H, s), 1.48 (3H, s), 3.19 (2H, ABq), 3.99 (1H, t, J 8.7 Hz), 5.20 (1H, d, J 17.3 Hz), 5.33 (1H, d, J 11 Hz), 5.75 (1H, d, J 8.4 Hz), 6.45 (1H, dd, J 17.3 and 11 Hz); MS (+ve ion electrospray) m/z 520 (MH$^+$, 100%).

EXAMPLE 24

Mutilin 14-(quinuclidin-4-yl)-acetate

Step 1. Quinuclidin-4-ylmethanol

Quinuclidine-4-carboxylic acid hydrochloride (6.0 g, 0.03 1 mmoles) in tetrahydrofuran (300 ml) was treated with lithium aluminum hydride (5.0 g, 0.137 mmoles) at ambient temperature for 18 hours. Water (20 ml) and 10% aqueous sodium hydroxide (7.5 ml) was added carefully and the mixture filtered, washing with diethyl ether. The combined filtrates were evaporated to dryness to give the title compound as a white solid 4.04 g, (91%): MS (+ve ion electrospray) m/z 142 (MH$^+$, 100%)

Step 2. Quinuclidin-4-ylacetonitrile

Quinuclidin-4-ylmethanol (2.19 g 0.015 moles) was converted to the corresponding, mesylate by treatment with triethylamine/methanesulphonyl chloride in chloroform. Washing the organics with saturated potassium carbonate, drying over sodium sulphate and evaporation to dryness gave the mesylate 3.24 g (95%). The mesylate was dissolved in dry dimethyl formamide (50 ml) and treated with sodium cyanide (2.26 g, 0.046 moles) and heated to 130° C. for 18 hours. The mixture was evaporated to dryness and the residue partitioned between saturated potassium carbonate and chloroform. The organics were dried ($Na_2SO_4$) and chromatographed on silica gel eluting with 0–10% methanol/chloroform. This gave the title compound 1.1 g (50%); $^1$H NNR ($CDCl_3$) 1.45 (6H, t, J 9 Hz), 2.12 (2H, s), 2.85 (6H, t, J 9 Hz); MS (+ve ion electrospray) m/z 151 ($MH^+$, 100%).

Step 3. Ethyl quinuclidin-4-ylacetate

Hydrogen chloride gas was bubbled through a solution of quinuclidin-4-ylacetonitrile (1.1 g, 0.007 moles) in ethanol (40 ml) at reflux for 48 hours. The mixture was concentrated in vacuo and treated with saturated potassium carbonate. Extraction with chloroform (4×50 ml), drying and chromatography on silica gel elutin with 0–10% methanol/chloroform gave the title compound 1.0 g (69%); $^1$H NMR ($CDCl_3$) 1.25 (3H, t, J 8 Hz), 1.45 (6H, t, J 9 Hz), 2.08 (2H, s), 2.85 (6H, t, J 9 Hz), 4.05 (2H, q, J 8 Hz).

Step 4. Quinuclidin-4-ylacetic acid hydrochloride

Ethyl quinuclidin-4-ylacetate (1.0 g, 0.005 moles) was heated under reflux in 5M hydrochloric acid (60 ml) for 18 hours. Evaporation to dryness and trituration with acetone gave the title compound 0.93 g (89%) $^1$H NMR ($CD_3SOCD_3$) 1.71 (6H, t, J 9 Hz), 2.15 (2H, s), 3.05 (6H, t, J 9 Hz), 10.35–10.55 (1H, br s), 12.19–12.29 (1H, br s).

Step 5. Quinuclidin-4-ylacetyl chloride hydrochloride

Quinuclidine-4-acetic acid hydrochloride (0.5 g, 0.0024 moles) was converted to the title compound using the method of Example 8, Step 4. MS (+ve ion electrospray in methanol) m/z 183 ($MH^+$ for methyl ester, 100% showing complete conversion).

Step 6. (3R)-3-Deoxo-11-deoxy-3-methoxy-11-oxo-4-epimutilin 14-(quinuclidin-4-yl)-acetate Quinuclidin-4-ylacetyl chloride hydrochloride (0.54 g, 0.0024 moles) and (3R)-3-deoxo-11-deoxy-3-methoxy-11-oxo-4-epimutilin (0.84 g, 0.0025 moles) were heated together in dry dimethylformamide (15 ml) at 100° C. for 6 hours. The mixture was evaporated to dryness and the residue partitioned between saturated sodium hydrogen carbonate and chloroform. The organic layer was dried and chromatographed on silica gel eluting with 0–6% methanol/chloroform to give the title compound 0.4 (39%) as a foam; $^1$H NMR ($CDCl_3$) 0.87 (3H, d, J 7 Hz), 0.98 (3H, d, J 7 Hz), 1.05–1.70 (19 H, m), 1.95–2.03 (2H, m), 2.15 (2H, d, J 5 Hz), 2.17–2.21 (1H, m), 2.35–2.45 (1H, m), 2.85–2.97 (8H, m), 3.15 (3H, s), 3.35–3.45 (1H, m), 4.95 (1H, d, J 17 Hz), 5.30 (1H, d, J 12 Hz), 5.70 (1H, d, J 12 Hz), 6.67 (1H, dd, J 17 Hz and J 10 Hz); MS (+ve ion electrospray) m/z 486 ($MH^{30}$, 100%).

Step 7. Mutilin 14-(quinuclidin-4-yl)-acetate (3R)-3-Deoxo-11-deoxy-3-methoxy-11-oxo-4-epimutilin-14-(quinuclidin-4-yl)-acetate (0.37 g, 0.008 moles) in 1,4-dioxan (5 ml) was treated with concentrated hydrochloric acid (5 ml) and stirred at ambient temperature for 4 hours. Water (20 ml) was added and the mixture basified with sodium hydrogen carbonate. The product was extracted into chloroform (2×25 ml), dried ($Na_2SO_4$) filtered and evaporated to dryness to give the title compound as a white foam 0.33 (92%), $^1$H NMR ($CDCl_3$) inter alia 0.7 (1H, d, J 7 Hz), 0.85 (1H, d, J 7 Hz), 1.1 (3H,s), 1.4 (3H, s), 2.85 (6H, t, J 9 Hz), 3.30–3.45 (1H, br s), 5.18 (1H, d, J 17 Hz), 5.31 (1H, d, J 10 Hz), 5.75 (1H, J, 10 Hz), 6.50 (1dd, J 17 and 10 Hz). MS (+ve ion electrospray) m/z 472 ($MH^+$, 100%).

EXAMPLE 25

Mutilin 14-(quinuclidin-4-ylmethyl)-aminoacetate

Step 1. 4-Cyanoquinuclidine

Quinuclidin-4-ylcarbonylchloride hydrochloride (Example 8, Step 4) (3.4 g 0.016 moles) was dissolved in acetonitrile (150 ml) and treated with 35% ammonia solution (50 ml). The mixture was stirred for 18 hours at ambient temperature then concentrated to dryness in vacuo. 1 g of the residue was then treated with phosphoms oxychloride (8 ml) at reflux for 5 hours. The mixture was then concentrated in vacuo and the residue partitioned between saturated potassium carbonate and diethylether (4×50 ml). The combined organic extracts were dried ($Na_2SO_4$), filtered and concentrated. Column chromatography on silica gel elutin with 0–5% methanol/chloroform gave the title compound 0.34 g (75%); 1H NMR ($CDCl_3$) 1.85 (6H t, J 10 Hz), 2.91 (6H, t, J 10 Hz).

Step 2. 4- Aminomethylquinuclidine

4- Cyanoquinuclidine (0.31 g, 0.0028 moles) was reduced with lithium aluminium hydride (0.45 g, 0.012 moles) in tetrahydrofuran (20 ml) at ambient temperature for 18 hours. Diethyl ether (20 mls) was added followed by water (1.8 ml) and 10%w/v aqueous sodium hydroxide (0.68 ml) and the mixture stirred for 30 minutes. The mixture was then filtered and the filtrate concentrated in vacuo to give the title compound 0.3 g (94%).

Step 3. Mutilin 14-(quinuclidin-4-ylmethyl)-aminoacetate

4-Aminomethylquinuclidine (0.2 g, 0.0014 moles) in chloroform (20 ml) was treated with diisopropylethylamine (0.54 g, 0.0042 moles) and mutilin 14-methane sulphonyloxyacetate (0.65 g, 0.0014 moles). The mixture was heated under reflux for 4 hours then allowed to cool. The solution was washed with saturated sodium hydrogen carbonate solution (2×20 ml). The organic phase was separated and dried ($Na_2SO_4$) and concentrated. Chromatography on a Sep-Pak silica gel (10 g) cartridge eluting with 0–10% (9:1 methanol/35% ammonia solution) in chloroform gave the title compound 0.0065 g (1%); $^1$H NMR ($CDCl_3$) inter alia 0.71 (3H, d, J 7 Hz), 0.89 (3H, d, J 7 Hz), 1.1 (3H, s), 1.41 (3H, s), 2.80 (6H, t, J 10 Hz), 3.28 (2H, q, J 1 Hz), 5.20 (1H, d, J 17 Hz), 5.35 (1H, d, J 11 Hz), 5.75(11H, d, J 8 Hz), 6.52 (1H, dd, J 17 and 11 Hz), MS (+ve ion electrospray) m/z 501 ($MH^+$, 30%).

EXAMPLE 26

Mutilin 14-[3-(quinuclidin-4-yl)-acrylate]

Step 1. N',O-Dimethylquinuclidin-4-yl amide

Quinuclidin-4-ylcarbonylchloride hydrochloride (Example 8, Step 4) (16.5 g, 0.079 moles) in acetonitrile (600 ml) at 0° C. was treated with N,O-Dimethylhydroxylamine hydrochloride (8.8g, 0.09 moles) and pyridine (20 ml. 0.24 moles) and stirred at ambient temperature for 18 hours. The mixture was concentrated in vacuo and the residue partitioned between saturated potassium carbonate and diethyl ether. The organics were dried ($Na_2SO_4$) filtered and evaporated to dryness to give the title compound 8.8 g (57%); $^1$H NMR ($CDCl_3$) 1.88 (6H, t, J 10 Hz), 2.91 (6H, t, J 10 Hz), 3.13 (3H, s), 3.65 (3H, s), Step 2. Quinuclidine-4-carboxaldehyde N,O-Dimethytquinuclidin-4-yl amide (8.77 g 0.044 moles) in dry toluene at −70° C. was treated with 1.5 molar diisobutylaluminiumhydride (45 ml, 0.067 moles) and allowed to warm to ambient temperature over 2 hours. The reaction was quenched with excess 5M hydrochloric acid, basified with potassium carbonate and extracted into diethyl ether. The organics were dried ($Na_2SO_4$), filtered and concentrated.

Chromatography on silica gel elutina with 0–10% (9:1 methanol/880 ammonia) in chloroform gave the title compound 1.3g (21%); $^1$H NMR (CDCl$_3$) 1.59 (6H, t, J 10 Hz), 2.90 (6H, t, J 10 Hz), 9.40 (1H, s).

Step 3. Ethyl [3-(quinuclidin-4-yl)-acrylate]

Triethylphosphonoacetate (1.6 ml, 0.0077 moles) in dimethoxyethane (50 ml) was treated with sodium hydride 60% dispersion in oil (0.35 g, 0.0088 moles) at ambient temperature for 1 hour. Quinuclidine-4-carboxaldehyde (1.0 g, 0.0072 moles) was then added and the mixture heated under reflux for 2 hours, allowed to cool and concentrated in vocuo. Chromatography of the residue on silica-gel, eluent as in Step 2, gave the title compound 0.71 g (47%); $^1$H NMR (CDCl$_3$) 1.29 (3H, t, J 10 Hz), 1.55 (6H, t, J 10 Hz), 2.99 (6H, t, J 10 Hz), 4.18 (2H, q, J 10 Hz), 5.65 (1H, d, J 19 Hz), 6.79 (1H, d, J 19 Hz).

Step 4. 3-(Quinuclidin-4-yl)-acrylic acid hydrochloride

Ethyl 3-(quinuclidin-4-yl)-acrylate (0.7 g, 0.0033 moles) was heated under reflux in 5 molar hydrochloric acid (30 ml) for 18 hours, cooled then concentrated in vacuo to an oil. Trituration with acetone gave the title compound as an off-white solid 0.43 g (60%). MS (+ve ion electrospray) m/z 182 (MH$^+$, 100%).

Step 5. 3-(Quinuclidin-4-yl)-acryloyl chloride hydrochloride

The title compound was prepared from 3-(quinuclidin-4-yl)-acrylic acid as in the method of Example 8. Step 4 (0.24g, 100%). MS (+ve ion electrospray) m/z 196 (MH$^+$, 100%-methyl ester from reaction with methanol).

Step 6. (3R)-3-Deoxo-11-deoxy-3-methoxy-11-oxo-4-epimutilin-14-[3'-(quinuclidin-4-yl)-acrylate]

3-(Quinuclidin-4-yl)acryloyl chloride (0.24 g 0.001 moles) and (3R)-3-deoxo-11-deoxy-3-methoxy-11-oxo-4-epimutilin (0.34 g, 0.001 moles) were heated together in dimethylformamide (15 ml) at 110° C. for 18 hours. The mixture was allowed to cool and concentrated in vacuo. The residue was partitioned between chloroform and saturated sodium hydrogen carbonate solution. The organic layer was dried (Na$_2$SO$_4$), filtered and evaporated to dryness. Chromatography on Sep-Pak silica gel 10 g cartridge eluting with 0–10% (9:1 methanol/35% ammonia solution) in chloroform gave the title compound 0.035 g (6.5%): MS (+ve ion electrospray) m/z 498 (MH$^+$, 100%).

Step 7. Mutilin 14-[3-(quinuclidin-4-yl)-acrylate]

The title compound was prepared from (3R)-3-Deoxo-11-deoxy-3-methoxy-11-oxo-4-epimutilin-14-[3'-(quinuclidin-4-yl)-acrylate] (0.035 g, 0.00007 moles) as in the method of Example 24, Step 7 0.026 g, (76%); $^1$H NMR (CDCl$_3$) inter alia 0.61 (3H, d, J 7 Hz), 0.8 (3H, d, J 7 Hz), 1.1 (3H, s), 2.80 (6H, t, J 10 Hz), 5.12 (1H. d, J 17 Hz), 5.28 (1H, d, J 11 Hz), 5.49 (1H, d, J 15 Hz), 5.70 (1H, d, J 8 Hz), 6.49 (1H, dd, J 17 and 11 Hz), 6.64 (1H, d, J 15 Hz); MS (+ve ion electrospray) m/z 484 (MH$^+$, 85%).

EXAMPLE 27

Mutilin 14-[3-(Quinuclidin-4-yl)]-propionate

Step 1. 3-(Quinuclidin-4-yl)-propionic acid hydrochloride 3-(Quinuclidin-4-yl)-acrylic acid (Example 26, Step 4) (0.2 g, 0.0009 moles) was hydrogenated at atmospheric pressure and ambient temperature over 10% palladium on charcoal (0.05 g) for 18 hours. The catalyst was filtered off and the filtrate evaporated to dryness to give the title compound 0.18 g (89%); MS (+ve ion electrospray) m/z 184 (MH$^+$, 100%).

Step 2. 3-(Quinuclidin-4-yl)-propionylchloride hydrochloride

The title compound was prepared from 3-(quinuclidin-4-yl)-propionic acid hydrochloride (0.18 g, 0.0008 moles) as in the method of Example 8, Step 4 0.19 g (100%). MS (+ve ion electrospray) m/z 198 (MH$^+$, 100%)-methyl ester from reaction with methanol).

Step 3. (3R)-3-Deoxo-11-deoxy-3-methoxy-11-oxo-4-epimutilin 14-[3'-(quinuclidin-4-yl)-propionatel The title compound was prepared from 3-(quinuclidin4-yl)-propionyl chloride hydrochloride (0.19 g, 0.0008 moles) and (3R)-3-deoxo-11-deoxy-3-methoxy-11-oxo-4-epimutilin (0.27 g, 0.0008 moles) as in the method of Example 24, Step 6 0.19 g (48%). MS (+ve ion eiectrospray) m/z 500 (MH$^+$, 100%).

Step 4. Mutilin 14-[3'-(quinuclidin-4-yl)-propionate]

The title compound was prepared from (3R)-3-deoxo-11-deoxy-3-methoxy-11-oxo-4-epimutilin 14-[3'-(quinuclidin-4-yl)-propionate] (0.18 g, 0.0004 moles) as in the method of Example 24. Step 7 0.15 g (83%); $^1$H NMR (CDCl$_3$) inter alia 0.69 (3H, d, J 7 Hz), 0.87 (3H, d, J 7 Hz), 1.15 (3H, s), 1.45 (3H, s), 2.85 (6H, t, J 10 Hz), 5.17 (1H, d, J 17 Hz), 5.33 (1H, d, J 11 Hz), 5.69 (1H, d, J 8 Hz), 6.51 (1H, dd, J 17 and 11 Hz), MS (+ve ion electrospray) m/z 486 (MH$^+$, 100%).

EXAMPLE 28

Mutilin 14-(quinuclidin-4-ylmethyloxy)-acetate

Step 1. Quinuclidin-4-ylmethanol

Quinuclidine-4-carboxylic acid hydrochloride (3.0 g, 0.016 moles) was treated with lithium aluminium hydride (2.5 g, 0.066 moles) in tetrahydrofuran (150 ml) at ambient temperature for 18 hours. The reaction was worked up as in the method of Example 25 Step 1 to give the title compound 2.24 g (100%). MS (+ve electrospray) m/z 142 (MH$^+$, 100%).

Step 2. Mutilin 14-(quinuclidin-4-ylmethyloxy)-acetate

Quinuclidin-4-ylmethanol (0.3 g, 0.002 moles) in dry dimethylformamide (5 ml) was treated with sodium hydride 60% dispersion in oil (0.095 g, 0.0022 moles) at ambient temperature for 1 hour. The mixture was then cooled to −10° C. and mutilin 14-methane-sulphonyloxyacetate (1.0 g, 0.002 moles) was added. The mixture was stirred for 4 hours at ambient temperature then concentrated in vacuo. The residue was partitioned between saturated sodium hydrogen carbonate and chloroform. The organic layer was dried (Na$_2$SO$_4$) filtered and evaporated to dryness. Chromatography on Sep-Pak silica cel (10 g) cartridge eluting with 0–10% (9:1 methanol/880 ammonia) in chloroform gave the title compound 0.12 g (12%); $^1$H NMR (CDCl$_3$) inter alia 0.71 (3H, d, J 7 Hz), 0.88 (3H, d, J 7 Hz), 1.15 (3H, s), 1.40 (3H, s), 2.85 (6H, t, J 10 Hz), 3.14 (2H, dd, J 10 and J 2.6 Hz), 3.93 (2H, q, J 17 Hz), 5.19 (1H d, J 17 Hz), 5.35 (1H, d, J 11 Hz), 5.82 (1H, d, J 8 Hz), 6.52 (1H, dd, J 17 and J 11 Hz), 5.82 (1H, d, J 8 Hz), 6.52 (1H, dd, J 17 and J 11 Hz). MS (+ve ion electrospray) m/z 502 (MH$^+$, 100%).

EXAMPLE 29

Mutilin 14-[(3R)-quinuclidin-3-ylaminol-acetate

The title compound was prepared from (R)-(+)-3-aminoquinuclidine dihydrochloride and mutilin 14-methanesulphonyloxyacetate as in the method of Example 28 Step 2 0.05 g (9%); $^1$H NMR (CDCl$_3$) inter alia 0.72 (3H, d, J 7 Hz), 0.88 (3H, d, J 7 Hz), 1.18 (3H, s), 1.45 (3H, s), 5.20 (1H, d, J 17 Hz), 5.35 (1H, d, J 11 Hz), 5.78 (1H, d, J 8 Hz), 6.52 (1H, dd, J 17 and J 11 Hz). MS (+ve ion electrospray) m/z 487 (MH$^+$, 82%).

EXAMPLE 30

Mutilin 14-(quinuclidin-4-yl-amino)-acetate

Step 1. 4- Aminoquinuclidine dihydrochloride

Quinuclidin-4-ylcarbonylchloride (Example 8, Step 4) (1.0 g, 0.0048 moles) was treated with sodium azide (0.34 g, 0.005 moles) in dimethylformamide (10 ml) at 50° C. for 18 hours. The mixture was concentrated in vacuo and the residue partitioned between saturated potassium carbonate and toluene. The toluene solution was separated, dried ($Na_2SO_4$), filtered and the filtrate was heated under reflux for 1 hour to give the isocyanate. The mixture was allowed to cool and then extracted with 5 M hydrochloric acid (3×20 ml). The combined acid extracts were then heated under reflux for 1 hour, cooled then evaporated to dryness. Trituration with acetone gave the title compound as a white solid 0.56 g (60%). M.S. (+ve ion electrospray) m/z 127 ($MH^+$, 100%).

Step 2. Mutilin 14-(quinuclidin-4-ylamino)-acetate

The title compound was prepared from 4-aminoquinuclidine dihydrochloride and mutilin 14-methanesulphonyloxyacetate as in the method of Example 28 Step 2 0.023 g (3%); $^1H$ NMR ($CDCl_3$) inter alia 0.7 (3H, d, J 7 Hz), 0.88 (3H, d, J 7 Hz), 1.17 (3H, s), 1.48 (3H, s), 2.95 (6H, t, J 10 Hz), 5.20 (1H, d, J 17 Hz), 5.35 (1H, d, J 11 Hz), 5.75 (1d, J 8 Hz), 6.49 (1H, dd, J 17 and J 11 Hz), M.S. (+ve ion electrsospray) m/z 487 ($MH^+$, 100%).

EXAMPLE 31

Mutilin 14-[4-(quinuclidin-4-yl)]-butyrate

Step 1. Quinuclidine-4-acetonitrile

Quinuclidin-4-ylmethanol (1.94 g, 0.014 moles) was converted to the corresponding mesylate by treatment with methane sulphonyl chloride and triethylamine in chloroform. The mesylate was dissolved in dimethylformamide (50 ml) and treated with sodium cyanide (1.4 g, 0.028 moles) at 120° C. for 18 hours. The mixture was cooled and concentrated in vacuo. The residue was partitioned between saturated potassium carbonate and chloroform. The organic layer was separated and dried ($Na_2SO_4$), filtered and evaporated to dryness. Chromatography on silica gel eluting with 0–10% methanol/chloroform gave the title compound 1.5 g (72%). M.S. (+ve electrospray) m/z 151 ($MH^+$, 100%).

Step 2. Quinuclidine-4-acetaldehyde

Quinuclidin-4-ylacetonitrile (3.0 g, 0.02 moles) in dry toluene (100 ml) was treated with 1.5 molar diusobutyl aluminium hydride (19.7 ml, 0.03 moles) at ambient temperature for 5 hours. The mixture was quenched by adding 2 M hydrochloric acid (50 ml) and stirring for 30 minutes. The mixture was then basified with potassium carbonate and extracted with chloroform. The organics were separated, dried ($Na_2SO_4$), filtered and evaporated to dryness to give the title compound as an oil 2.2 g (72%). M.S. (+ve ion electrospray) m/z 154 ($MH^+$, 100%).

Step 3. Mutilin 14-[4-(quinuclidin-4-yl)]-butyrate

The title compound was prepared in 6 steps from quinuclidin-4-ylacetaldehyde analogously to Example 26 Steps 3–4 and Example 27 Steps 1–4 0.08 g (3% overall, 6 steps); $^1H$ NMR ($CDCl_3$) inter alia 0.65 (3H, d, J 7 Hz), 0.81 (3H, d, J 7 Hz), 1.10 (3H, s), 1.39 (3H, s), 2.95 (6H, t, J 10 Hz), 5.12 (1H, d, J 17 Hz), 5.27 (1H, d, J 11 Hz), 5.65 (1H, d, J 8 Hz), 6.43 (1H. dd, J 17 and J 11 Hz), M.S. (+ve electrospray) m/z 500 ($MH^+$, 100%).

EXAMPLE 32

(±) Mutilin 14-(1-azabicyclo[3,3,0]oct-4-ylmethylsulfanyl)-acetate

The title compound was prepared as in the method of Example 15 from (±)-1-azabicyclo[3,3,0]octan-4-ylmethanol (1.85 g, 0.007 moles) (Pizzomno, M. T., Albornico S. M., J. Org. Chem. (1974) 39, 731). This gave 1.3 g (71%); $^1H$ NMR ($CDCl_3$) inter alia 0.75 (3H, d, J 7 Hz), 0.88 (3H, d, J 7 Hz), 1.17 (3H, s), 1.45 (3H, s), 5.20 (1H, d, J 17 Hz), 5.35 (1H, d, J 11 Hz), 5.75 (1H, d, J 8 Hz), 6.50 (1H, dd, J 17 and 11 Hz), M.S. (+ve ion electrospray) m/z 518 ($MH^+$, 100%).

EXAMPLE 33

(±) Mutilin 14-(1-azabicyclo[3,3,0]oct-3-ylsulfanyl)-acetate

The title compound was prepared as in the method of Example 15 from (±)-1-azabicycto[3,3,0]octan-3-ol (0.6 g, 0.0047 moles) (Schnekenburger, J. Pharm. Inst., Univ. Kiel, Kiel. D-2300. Fed. Rep. Ger. Arch. Pharm. (1988), 321(12), 925–9). This Dave 0.21 g (9%); $^1H$ NMR ($CDCl_3$) inter alia 0.72 (3H, d, J 7 Hz), 0.88 (3H, d, J 7 Hz), 1.18 (3H, s), 1.45 (3H, s), 5.20 (1H, d, J 17 Hz), 5.34 (1H, d, J 11 Hz), 5.74 (1H, d, J 8 Hz), 6.46 (1H, dd, J 17 and J 11 Hz). M.S. (+ve ion electrospray) m/z 504 ($MH^+$, 35%).

EXAMPLE 34

Mutilin 14-(endo 8-methyl-8-azabicyclo[3,2,1]oct-3-ylsulfanyl)-acetate

The title compound was prepared as in the method of Example 15 from exo 8-methyl-8-azabicyclo[3,2,1]octan-3-ol (1.8 g, 0.0127 moles) (Nickon, A., Fieser, L. F., J. American. Chem. Soc. (1952) 74. 5566). This gave 0.1 g (.5%); $^1H$ NMR ($CDCl_3$) inter alia 0.73 (3H, d, J 7 Hz), 0.88 (3H, d, J 7 Hz), 1.17 (3H, s), 1.47 (3H, s), 5.18 (1H, d, J 17 Hz), 5.32 (1H, d, J 11 Hz), 5.75 (1H, d, J 8 Hz), 6.47 (1H, dd, J 17 and 11 Hz), M.S. (+ve ion electrospray) m/z 518 ($MH^+$, 100%).

EXAMPLE 35

(±) Mutilin 14-(1-azabicyclo[4,3,0]non-4-ylsulfanyl)-acetate

Step 1. (±) 1-Azabicyclo[4,3,0]nonan-4-ol

1-Azabicyclo[4,3,0]nonan-4-one (1.0 g, 0.0072 moles) (King, F. D., J. Chem. Soc. Perkin. Trans. 1, (1986) 447) in tetrahydrofuran (50 ml) was treated with lithium aluminium hydride (0.7 g. 0.0185 moles) at ambient temperature for 18 hours. Work up in the usual way gave the title compound 1.0 g (100%). M.S. (+ve ion electrospray) m/z 142 ($MH^{30}$, 95%).

Step 2. (±) Mutilin 14-(1-azabicyclo[4,3,0]non-4-ylsulfanyl)-acetate

The title compound was prepared as in the method of Example 15 from (±) 1-Azabicyclo[4,3,0]nonan-4-ol (1.0 g, 0.0072 moles). This gave 1.12 g (28%); $^1H$ NMR ($CDCl_3$) inter alia 0.72 (3H, d, J 7 Hz), 0.88 (3H, d, J 7 Hz), 1.20 (3H, s), 1.47 (3H, s), 5.21 (1H, d, J 17 Hz), 5.34 (1Hd, J 11 Hz), 5.77 (1H, d, J 8 Hz), 6.48 (1H, dd, J 17 and 11 Hz). M.S. (+ve ion electrospray) m/z 518 ($MH^+$, 100%).

EXAMPLE 36

(±) 19,20-Dihydromutilin 14-(1-azabicyclo[4,3,0]non-4-ylsulfanyl)-acetate

The title compound was prepared as in the method of Example 15 from (±) 1-azabicyclo[4,3,0]nonan-4-ol (0.66 g, 0.0047 moles) and 19,20-dihydromutilin 14-methanesulphonyloxyacetate (2.43 g, 0.0047 mmoles) to give 0.44 g (18%); $^1$H NMR (CDCl$_3$) inter alia 0.71 (3H, d, J 7 Hz), 0.8 (3H, t, J 9 Hz), 1.45 (3H, s), 3.15 (2H, s), 5.65 (1H, d, J 8 Hz). M.S. (+ve ion electrospray) m/z 520 (MH$^+$, 100%).

EXAMPLE 37

Mutilin 14-(1-carboxymethylpiperidin-4-ylsulfanyl)-acetate

Step 1. tert-Bu tyl (piperidin-4-one-1-yl)-acetate

4-Piperidone monohydrate hydrochloride (5 g, 0.033 moles) was treated with tert-butylbromoacetate (6.98 g, 0.037 moles) and potassium carbonate (13.65 g, 0.099 moles) in dimethylformamide (100 ml) at 100° C. for 24 hours. The mixture was cooled and concentrated in vacuo. The residue was partitioned between saturated potassium carbonate solution and diethyl ether (2×50 ml). The combined organic layers were dried (Na$_2$SO$_4$), filtered and evaporated to dryness to give the title compound 7.36 g (94%) $^1$H NMR (CDCl$_3$) 1.45 (9H, s), 2.45 (4H, t, J 7 Hz), 2.3–2.4 (4H, m), 3.29 (2H, s).

Step 2. tert-Butyl (piperiditi-4-ol-1-yl)-acetate tert-Butyl (piperidin-4-one-1-yl)-acetate (3 g, 0.014 moles) was treated with sodium borohydride (1.13 g, 0.028 moles) in methanol (150 ml) at ambient temperature for 1 hour. Glacial acetic acid (1.68 g, 0.028 moles) was added and the mixture stirred for 15 minutes. The mixture was concentrated in vacuo and the residue partitioned between saturated sodium carbonate and ethyl acetate. The organics were separated, dried (Na$_2$SO$_4$), filtered and evaporated to dryness to give the title compound (2.9g, 96%). M.S. (+ve ion electrospray) m/z 216 (MH$^+$, 100%).

Step 3. Mutilin (1-carboxymethylpiperidin-4-ylsulfanyl)-acetate

The title compound was prepared as in the method of Example 15 from tert-buty(piperidin-4-ol-1-yl)-acetate (1.5 g, 0.007 moles). The tertbutyl ester group is hydrolysed in the workup. This gave 0.3 (8%); $^1$H NMR (CDCl$_3$) inter alia 0.7 (3H, d, J 7 Hz), 0.88 (3H, d, J 7 Hz), 1.17 (3H, s), 1.47 (3H, s), 5.22 (1H, d, J 17 Hz), 5.35 (1H, d, J 11 Hz), 5.75 (1H, d, J 8 Hz), 6.45 (1 H, dd, J 17 and 11 Hz), M.S. (+ve ion electrospray) m/z 536 (MH$^+$, 100%).

EXAMPLE 38

Mutilin 14-(piperidin-4-ylsulfanyl)-acetate

Step 1. 1(tert-Butoxycarbonyl)piperidin-4-ol

1(tert-Butoxycarbonyl)-4-piperidone (5 g, 0.025 moles) was treated with sodium borohydride (1.89 g, 0.05 moles) as in the method of Example 37, Step 2 to give the title compound 5.07 g (100%); $^1$H NMR (CDCl$_3$) inter alia 1.45 (9 H, s), 1.29–1.41 (2 H, m), 2.42–3.05 (2H, m), 3.75–3.99 (3H, m).

Step 2. Mutilin 14-(1-tertbutoxycarbonylpiperid-4-ylthio)-acetate

The title compound was prepared as in the method of Example 15 from 1-(tert-butoxycarbonyl)piperidin-4-ol (2.5 g, 0.012 moles). M.S. (-ve ion electrospray) m/z 576 (M-H, 100%).

Step 3. Mutilin 14-(piperidin-4-ylsulfanyl)-acetate

The product from Step 2 was treated with trifluoroacetic acid (10 ml) in dichloromethane (100 ml) at 0° C. for 2 hours. The mixture was concentrated in vacuo and the residue partitioned between saturated sodium hydrogen carbonate and chloroform. The organic layer was separated, dried (Na$_2$SO$_4$) filtered and evaporated to dryness. Chromatography on silica gel eluting with 0–1 0% (9:1 methanol/ 880 ammonia) in chloroform gave the title compound 1.01 g (26%); $^1$H NMR (CDCl$_3$) inter alia 0.75 (3H, d, J 7 Hz), 0.9 (3H, d, J 7 Hz), 1.18 (3H, s), 1.45 (3H, s), 5.20 (1H, d, J 17 Hz), 5.35 (1H, d, J 11 Hz), 5.80 (1H, d, J 8 Hz), 6.52 (1H, dd, J 17 and 11 Hz). M.S. (+ve ion electrospray) m/z 478 (MH$^+$, 65%).

EXAMPLE 39

Mutilin 14-(1-methylpiperidin-4-ylmethylsulfanyl)-acetate hydrochloride

Step 1. 1-Methyl-4-(hydroxymethyl)piperidine

1-Methylpiperidine-4-carboxylic acid hydrochloride (J. Med. Chem. 1988, 31. 812) (1 g, 0.007 mole) was added portionwise to a suspension of lithium aluminium hydride (1.3 g 0.035 mole) in dry tetrahydrofuran (100 ml) under argon at 0° C. The mixture was heated under reflux overnight after which it was cooled to 0° C. and treated dropwise with water (1.3 ml). 10% sodium hydroxide solution (1.95 ml) and water (3.25 ml) and stirred for 1 hour at room temperature. The resulting slurry was filtered through celite and the filtrate evaporated in vacuo to afford the title compound 0.90 g (99.7%) as a pale orange oil; $^1$H NMR (CDCl$_3$) 1.18–1.53 (3H, m), 1.67–1.81 (2H, m), 1.83–2.12 (3H, m), 2.28 (3H, s), 2.79–2.94 (2H, m), 3.50 (2H, d, J 7 Hz); MS (+ve ion electrospray) m/z 130 (MH$^+$).

Step 2. (1-Methylpiperidin-4-ylmethylsulfanyl)-acetate

Triphenylphosphine (3.67 g, 0.014 mole) was dissolved in dry tetrahydrofuran (25 ml) and cooled to 0° C. under argon. Diisopropyl azodicarboxylate (2.75 ml, 0.014 mole) was added dropwise and the mixture was stirred at 0° C. for 0.5 hour. The product of Step 1 (0.90 g, 0.007 mole) and thiolacetic acid (1.0 ml, 0.014 mole) in dry tetrahydrofuran (50 ml) were added dropwise and the mixture stirred at room temperature overnight. The solvent was removed in vacuo and the residue was partitioned between 1M hydrochloric acid and diethyl ether. The aqueous layer was washed with diethyl ether until all triphenylphosphine oxide had been removed, basified with solid potassium carbonate, extracted into dichloromethane, dried (magnesium sulfate) and evaporated in vacuo to afford the title compound 0.60 g (46%) as a pale yellow oil; $^1$H NMR (CDCl$_3$) 1.22–1.59 (3H, m), 1.72–1.85 (2H, m), 1.95 (2H, dt, J 13 and 3 Hz), 2.28 (3H, s), 2.35 (3H, s), 2.80–1.85 (2H, m), 1.95 (2H, dt, J 13 and 3 Hz), 2.28 (3H, s), 2.35 (3H, s), 2.80–2.98 (4H, m); MS (+ve ion electrospray) m/z 188 (MH$^+$).

Step 3. Mutilin 14-(1-methylpiperidin-4-ylmethylsulfanyl)-acetate hydrochloride

The product of Step 2 (0.19 g. 0.001 mole) was dissolved in dry ethanol (10 ml) under argon and treated with sodium methoxide (0.054 g, 0.001 mole). The mixture was stirred for 1 hour and mutilin 14-methanesulfonyloxyacetate (0.456 g, 0.001 mole) was added. The mixture was stirred at room temperature overnight. The solvent was removed in vacuo and the residue partitioned between water and dichloromethane. The organic layer was dried (magnesium sulfate) and evaporated in vacuo. The residue was purified by column chromatography, eluting with dichloromethane to 15% methanol/dichloromethane. The resulting gum was converted to the hydrochloride salt to afford the title compound 0.17 g (34%) as a white foam; $^1$H NMR (CDCl$_3$) inter alia 0.73 (3H, d, J 7 Hz), 0.90 (3H, d, J 7 Hz), 5.23 (1H, dd, J 17 and 3 Hz), 5.35 (1dd, J 13 and 3 Hz), 5.73 (1H, d, J 7 Hz), 6.48 (1H, q, J 17 and 10 Hz), 12.26–12.69 (1H, br s); MS (+ve ion electrospray) m/z 506 (MH$^+$free base).

EXAMPLE 40

Mutilin 14-{(3S,4R)-1-azabicyclo[2.2.1]hept-3-ylmethylsulfanyl}-acetate

Step 1. (3S,4R)-1-Azabicyclo[2.2.1]hept-3-ylmethanol

The title compound 0.60 g (84%) was prepared from (3S,4R)-1-azabicyclo[2.2.1]heptane-3-carboxylic acid hydrochloride (WO 98/05659, SmithKline Beecham) using the method of Example 1 Step 1; $^1$H NMR (CDCl$_3$) 1.38–1.65 (1H, m), 1.83–2.00 (1H, m), 2. 12–2.6 (7H, m), 2.78–3.05 (2H, m), 3.49–3.81 (2H, m); MS (+ve ion elcctrosprav) m/z 128 (MH$^+$).

Step 2. [(3S, 4R)-1-Azabicyclo[2.2.1]hept-3-ylmethylsulfanyl]-acetate

The title compound, 0.58g (66%) was prepared from the product of Step 1 using the method of Example 1 Step 2: $^1$H NMR (CDCl$_3$) 1.36–1.63 (2H, m), 1.90–2.01 (1H, m), 2.10–2.29 (1H, m), 2.34 (3H, s), 2.40–2.58 (4H, m), 2.78–2.96 (2H, m), 3.00–3.13 (2H, m), MS (+ve ion electrospray) m/z 186 (MH$^+$).

Step 3. Mutilin 14-{ (3S,4R)-1-azabicyclo[2.2.1]hept-3-ylmethylsulfanyl}-acetate The title compound, 0.21 g (42%) was prepared from the product of Step 2 using the method of Example 1 Step 3. Purification of the compound was achieved by flash column chromatography on silica gel eluting, with 10% methanol/dichloromethane; $^1$H NMR (CDCl$_3$) inter alia 0.76 (3H, d, J 7 Hz), 0.90 (3H, d, J 7 Hz), 3.13 (2H, s), 5.20 (1H, dd, J 18 and 2 Hz), 5.34 (1H, dd, J 12 and 2 Hz), 5.78 (1H, d, J 7 Hz), 6.51 (1H, q, J 18 and 13 Hz); MS (+ve ion electrospray) m/z 504 (MH$^+$).

EXAMPLE 41

Mutilin 14-(quinuclidin-2-ylmethylsulfanyl)-acetate

Step 1. (Quinuclidin-2-ylmethylsulfanyl)-acetate

The title compound. 0.78 g (55%) was prepared from quinuclidin-2-ylmethanol (J. Am. Chem. Soc., 1988, 116, 1278) using the method of Example 1 Step 2; $^1$H NMR (CDCl$_3$) 1.08–1.22 (1H, m), 1.40–1.58 (4H, m), 1.73–1.90 (2H, m), 2.35 (3H, s), 2.66–3.28 (7H, m); MS (+ve ion electrospray) m/z 158 (MH$^+$ thiol).

Step 2. Mutilin 14-(quinuclidin-2-ylmethylsulfanyl)-acetate

The title compound, 0.20 g (39%) was prepared from the product of Step 1 using the method of Example 1 Step 3; $^1$H NMR (CDCl$_3$) inter alia 1.75 (3H, d, J 7 Hz), 0.90 (3H, d, J 7 Hz), 3.18 (2H, d, J 7 Hz), 5.21 (1H, dd, J 18 and 2 Hz), 5.37 (1H, dd, J 12 and 2 Hz), 5.75 (1H, d, J 7 Hz), 6.50 (1H, q, J 18 and 12 Hz); MS (+ve ion electrospray) m/z 518 (MH$^+$).

EXAMPLE 42

Mutilin 14-(1-azabicyclo[2.2.1]hept-4-ylmethylsulfanyl)-acetate

Step 1. (1-Azabicyclo[2.2.1]hept-4-ylmethylsulfanyl)-acetate

The title compound. 0.55 g (42%) was prepared from 1-azabicyclo[2.2.1]hept-4-yl methanol (WO 93/15080) using the method of Example 1 Step 2; $^1$H NMR (CDCl$_3$) 1.21–1.35 (2H, m), 1.50–1.68 (2H, m), 2.29 (2H, s), 2.38 (3H, s), 2.53–2.70 (2H, m), 2.99–3.05 (2H, m), 3.28 (2H, s); MS (+ve ion electrospray) m/z 186 (MH$^+$).

Step 2. Mutilin 14-(1-azabicyclo[2.2.1]hept-4-ylmethylsulfanyl)-acetate

The title compound. 0.14 g, (28%) was prepared from the product of Step 1 using the method of Example 1 Step 3; $^1$H NMR (CDCl$_3$) inter alie 0.78 (3H, d, J 7 Hz), 0.90 (3H, d, J 7 Hz), 3.16 (2H, s)5.22 (1H, dd, J 18 and 2 Hz), 5.37 (1H, dd, J 12 and 2 Hz), 5.78 (1H, d, J 8 Hz), 6.50 (1H, q, J 18 and 12 Hz); MS (+ve ion electrospray) m/z 504 (MH$^+$).

EXAMPLE 43

Mutilin 14-{(3R,4S)-1-azabicyclo[2.2.1]hept-3-ylmethylsulfanyl}-acetate

Step 1. (3R, 4S)-1-Azabicyclo[2.2.1]hept-3-yl methanol

The title compound, 0.68 g (95%) was prepared from (3R,4S)-1-azabicyclo[2.2.1] heptane-carboxylic acid usin; the method of Example 1 Step 1; $^1$H NMR (CDCl$_3$) 1.37–1.71 (2H, m), 1.82–2.00 (1H, m), 2.10–2.72 (6H, m), 2.77–3.05 (2H, m), 3.47–3.76 (2H, m); MS (+ve ion electrospray) m/z 128 (MH$^+$).

Step 2. [(3R,4S)-1 -Azabicyclo[2.2.1]hept-3-ylmethylsulfanyl]-acetate

The title compound, 0.22 g (25%) was prepared from the product of Step 1 using the method of Example 1 Step 2; $^1$H NMR (CDCl$_3$) 1.40–1.70 (2H, m), 1.93–2.09 (1H, m), 2.12–2.31 (1H, m), 2.35 (3H, s), 2.51–2.70 (4H, m), 2.78–2.98 (2H, m), 3.0–3.15 (2H, m); MS (+ve ion electrospray) m/z 186 (MH$^+$).

Step 3. Mutilin 14-{(3R,4S)-1-azabicyclo[2.2.1]hept-3-ylmethylsulfanyl }-acetate The title compound 0.12 g. (20%) was prepared from the product of Step 2 using the method of Example 1 Step 3; $^1$H NMR (CDCl$_3$) inter alia 0.72 (3H, d, J 7 Hz), 0.89 (3H, d, J 7 Hz), 3.13(2H, s), 5.21 (1H, dd, J 18 and 2 Hz), 5.35 (1H, dd, J 12 and 2 Hz), 5.76 (1H, d, J 7 Hz), 6.50 (1H, q, J 18 and 12 Hz); MS (+ve ion electrospray) m/z 504 (MH$^+$).

EXAMPLE 44

Mutilin 14-(1-azabicyclo[3.2.1]oct-5-ylmethylsulfanyl)-acetate

Step 1. 1-Azabicyclo[3.2.1]oct-5-ylmethanol

The title compound, 2.05 g (93%) was prepared from 1-azabicyclo[3.2.1]octane-5-carboxylic acid hydrochloride (J. Med. Chem., 1991, 34, 2726–2735) using the method of Example 1 Step 1; $^1$H NMR (CDCl$_3$) 1.39–1.90 (5H, m), 2.61 (2H, s), 2.70 (4H, m), 3.35–3.75 (4H, m); MS (+ve ion electrospray) m/z 142 (MH$^+$).

Step 2. [1-Azabicyclo[3.2.1]oct-5-ylmethylsulfanyl]-acetate

The title compound, 1.0 g, (35%) was prepared from the product of Step 1 using the method of Example 1 Step 2; $^1$H NMR (CDCl$_3$) 1.45–1.89 (6H, m), 2.47 (3H, s), 2.60 (2H, s), 2.70–2.94 (3H, m), 3.00–3.17 (3H, m); MS (+ve ion eiectrospray) m/z 200 (MH$^+$)

Step 3. Mutilin 14-(1-azabicyclo[3.2.1]oct-5-ylmethylsulfanyl)-acetate

The title compound, 0. 19 g (7%) was prepared from the product of Step 2 using the method of Example 1 Step 3; $^1$H NMR (CDCl$_3$) inter alia 0.73 (3H, d, J 7 Hz), 0.90 (3H, d, J 7 Hz), 5.20 (1H, dd, J 18 and 2 Hz), 5.37 (1H, dd, J 12 and 2 Hz), 5.76 (1H. d, J 7 Hz), 6.48 (1H, q, J 18 and 12 Hz); MS (+ve ion electrospray) m/z 518 (MH$^+$).

EXAMPLE 45

Mutilin 14-{(R)-1-Methylpiperid-2-ylmethylsulfanyl}-acetate

Step 1. (R)-1-Ethylcarbamoylpiperidine-2-carboxylic acid

L-Pipecolinic acid (0.50 g, 0.004 mole) in dry dichloromethane (10 ml) was cooled to 0° C. under argon and treated with triethylamine (0.65 ml. 0.0046 mole) followed dropwise by ethyl chloroforrmate (0.37 ml, 0.004 mole) in dry dichloromethane (2 ml). The mixture was stirred overnight at room temperature after which it was diluted with dichloromethane, washed with 5M hydrochloric acid and the organic layer dried (magnesium sulfate) and evaporated in vacuo to afford the title compound 0.60 g (77%) as an orange oil; $^1$H NMR (CDCl$_3$) 1.12–1.84 (8H, m), 2.15–2.40 (1H, m), 2.88–3.20 (1H, m), 3.90–4.28 (3H, m), 4.77–5.07 (1H, m), 5.68–6.82 (1H, br s), Step 2. (R)-1-Methylpiperidin-2-ylmethanol The product of Step 1 (0.60 g, 0.003 mole) in dry tetrahydrofuran (10 ml) was added dropwise to a suspension of lithium aluminium hydride (0.57 g, 0.015 mole) in dry tetrahydrofuran (20 ml). The mixture was heated under reflux for 2 hours and stirred at room temperature overnight. The reaction mixture was cooled to 0° C. and water (0.5 ml) was added dropwise, followed by 10% sodium hydroxide solution (0.9 ml) and water (1.4 ml). The mixture was stirred for 1 hour, filtered through Celite and the filtrate evaporated in vacuo to afford the title compound 0.31 g (80%) as a pale yellow oil; $^1$H NMR (CDCl$_3$) 1.17–2.00 (8H, m), 2.14 (1H, dt, J 13 and 2 Hz), 2.30 (3H, s), 2.76–2.96 (1H, m), 3.40 (1H, dd, J 13 and 1 Hz), 3.88 (1H, dd, J 12 and 5 Hz); MS (+ve ion electrospray) m/z 130 (MH$^+$).

Step 3. [(R)-1-Methylpiperid-2-ylmethylsulfanyl]-acetate

The title compound, 0.30 g (71%) was prepared from the product of Step 2 using the method of Example 1 Step 2: $^1$H NMR (CDCl$_3$) 1.16–1.76 (6H, m), 2.00–2.18 (2H, m), 2.29 (13H, s), 2.35 (3H, s), 2.80–2.92 (1H, m), 3.00–3.23 (2H, m);

Step 4. Mutilin 14-{(R)-1-Methylpiperid-2-ylmethylsulfanyl}-acetate

The title compound, 0.19 g (22%) was prepared from the product of Step 3 using the method of Example 1 Step 3; $^1$H NMR (CDCl$_3$) inter alia 0.75 (3H, d, J 7 Hz), 0.89 (3H, d, J 7 Hz), 3.11 (2H, s), 3.36 (1H, q, J 12 and 7 Hz), 5.19 (1H, dd, J 18 and 2 Hz), 5.35 (1H, dd, J 12 and 2 Hz), 5.75 (1H, d, J 7 Hz), 6.50 (1H, q, J 18 and 12 Hz); MS (+ve ion electrospray) m/z 506 (MH$^+$).

EXAMPLE 46

Mutilin 14-{(S)-1-Methylpyrrolid-2-ylmethylsulfanyl}-acetate

Step 1. [(S)1-Methylpyrrolid-2-ylmethylsulfanyl]-acetate

The title compound, 0.64 g (85%) was prepared from (S)(−)-1-methyl-2-pyrrolid-2-ylmethanol using the method of Example 1 Step 29 1H NMR (CDCl$_3$) 1.44–1.61 (1H, m), 1.65–1.85 (2H, m), 1.87–2.04 (1H, m), 2.15–2.42 (2H, m), 2.35 (3H, s), 2.38 (2.38 (3H, s), 2.82–2.94 (1H, m), 3.05–3.14 (1H, m), 3.28 (1H, dd, J 13 and 3 Hz); MS (-ve ion electrospray) m/z 130 (M-H for thiol).

Step 2. Mutilin 14-{(S)-1-Methylpyrrolid-2-ylmethylsulfanyl}-acetate

The title compound, 0.17 g (23%) was prepared from the product of Step 1 using the method of Example 1 Step 3; $^1$H NMR (CDCl$_3$) inter alia 0.76 (3H, d, J 7 Hz), 0.90 (3H, d, J 7 Hz), 3.18 (2H, s), 3.35 (1H, q, J 10 and 7 Hz), 5.20 (1H, dd, J 18 and 2 Hz), 5.35 (1H, dd, J 12 and 2 Hz), 5.75 (1H, d, J 7 Hz), 6.50 (1H, q, J 18 and 12 Hz); MS (+ve ion electrospray) m/z 492 (MH$^+$).

EXAMPLE 47

Mutilin 14-{(R)-1-methylpiperid-3-ylmethylsulfanyl}-acetate

Step 1. (R)-Ethyl 1-ethylcarbamoylpiperidine-3-carboxylate
(R)-Ethylnipecotate (*J. Org. Chem.*, 56, 1991, 1166–1170) (3.0 g, 0.019 mole) in dry dichloromethane (50 ml) was cooled to 0° C. under argon. Triethylamine (3.19 ml, 0.023 mole) was added, followed dropwise by ethyl chloroformate (1.83 ml, 0.019 mole) in dry dichloromethane (6 ml) and the mixture was stirred overnight at room temperature. The reaction mixture was diluted with dichloromethane, washed with water, dried (magnesium sulfate) and evaporated in vacuo to afford the title compound 3.45 g (79%) as a colourless oil; $^1$H NMR (CDCl$_3$) 1.28 (6H, t, J 7 Hz), 1.38–1.82 (3H, m), 2.00–2.15 (1H, m), 2.38–2.55 (1H, m), 2.77–3.13 (2H, m), 3.91–4.04 (1H, m), 4.07–4.35 (5H, m).

Step 2. (R)1-Methylpiperid-3-ylmethanol

The title compound, 1.8 g, (92%) was prepared from the product of Step 1 using the method of Example 7 Step 2; $^1$H NMR (CDCl$_3$) 0.90–1.12 (1H, m), 1.50–1.90 (5H, m), 1.94–1.99 (1H, m), 2.25 (3H, s), 2.57–2.74 (1H, m), 2.79–2.92 (1H, m), 3.14–3.71 (3H, m); MS (+ve ion electrospray) m/z 130 (MH$^+$).

Step 3. [(R)-1-Methylpiperid-3-ylmethylsulfanyl]-acetate

The title compound, 0.59 g (81%) was prepared from the product of Step 2 using the method of Example 1 Step 2; $^1$H NMR (CDCl$_3$) 0.87–1.06 (1H, m), 1.44–1.94 (6H, m), 2.27 (3H, s), 2.34 (3H, s), 2.62–2.92 (4H, m); MS (+ve ion electrospray) m/z 188 (MH$^+$)

Step 4. Mutilin 14-{ (R)-1-methylpiperid-3-ylmethylsulfanyl}-acetate

The title compound, 0.26 (34%) was prepared from the product of Step 3 using the method of Example 1 Step 3; $^1$H NMR (CDCl$_3$) inter alia 0.74 (3H, d, J 7 Hz), 0.90 (3H, d, J 7 Hz), 3.12 (2H, d, J 2 Hz), 3.30–3.44 (1H, m), 5.22 (1H, dd, J 18 and 2 Hz), 5.38 (1H, dd, J 12 and 2 Hz), 5.76 (1H, d, J 7 Hz), 6.50 (1H, q. J 18 and 12 Hz), MS (+ve ion electrospray) m/z 506 (MH$^+$).

EXAMPLE 48

Mutilin 14-(quinuclidin-4-ylmethylsulfanyl)-acetate

A solution of triphenylphosphine (1.1 g, 0.0042 mole) in dry tetrahydrofuran (50 ml) was ice-cooled under argon and treated with diisopropyl azodicarboxylate (0.85 g, 0.0042 mole). After 30 minutes a solution of thiolacetic acid (0.315 ml. 0.0042 mole) and quinucildin-4-ylmethanol (0.565 g, 0.0042 mole) in dry tetrahydrofuran was added dropwise. The mixture was then allowed to stand at 5° C. for 72 hours. Following concentration in vacuo the residue was partitioned between diethyl ether and 1M hydrochloric acid. The aqueous phase was washed with diethyl ether then concentrated in vacuo to give a solid (0.65 g). The solid was dissolved in ethanol and treated with potassium tert-butoxide (0.785 g, 0.007 mole). After stirrin2 for 30 minutes mutilin 14-methanesulfonyloxyacetate (1.38 g, 0.003 mole) was added. The mixture was stirred under argon for 18 hours then concentrated in vacuo. The residue was partitioned between chloroform and water. The organic phase was washed with brine, dried over magnesium sulfate and concentrated in vacuo. Chromatography on silica gel eluting with chloroform/methaol/35% ammonia solution (10/1/0.1) provided the title compound 0.478 g (31%); $^1$H NMR (CDCl$_3$) inter alia 0.74 (3H, d, J 6.5 Hz), 0.88 (3H, d, J 6.7 Hz), 1.17 (3H, s), 1.40 (6H, t, J 8 Hz), 1.49 (3H, s), 2.47 (2H, s), 2.87 (6H, t, J 8 Hz), 3.0 (2H, s), 3.36 (1H, m), 5.1 to 5.4 (2H, m), 5.75 (1H, d, J 8.3 Hz), 6.48 (1H, m); MS (+ve ion electrospray) m/z 518 (MH$^+$, 100%).

EXAMPLE 49

Mutilin 14-(8-methyl-8-azabicyclo [3.2.1]oct-3-ylmethylsulfanyl)-acetate

Step 1. (8-methyl-8-azabicyclo[3.2.1]oct-3-yl)methanol

The title compound was prepared from 8-methyl-8-azabicyclo[3.2.1]octane-3-carboxylic acid hydrochloride salt (WO 98/05659 Example 25, Step 3) using the process described in Example 24 Step 1 0.78 g (100%); $^1$NMR (CDCl$_3$) inter alia 1.3–2.0 (9H, m), 2.25 (3H, s), 3.16 (2H, m), 3.44 (2H, d, J 6.3 Hz); MS (+ve ion electrospray) m/z 156 (MH$^+$, 100%).

Step 2. Mutilin 14-(8-methyl-8-azabicyclo[3.2.1]oct.3-ylmethylsulfanyl)-acetate

The title compound was prepared from (8-methyl-8-azabicyclo[3.2.1]oct-3-yl)methanol and mutilin 14-methanesulfonyloxyacetate using the process described in Example 15 0.101 g (19%); $^1$H NMR (CDCl$_3$) inter alia 0.74 (3H, d, J 6.5 Hz), 0.88 (3H, d, J 7.0 Hz), 1.25 (3H, s), 1.49 (3H, s), 2.34 (3H, s), 2.48 (2H, d,), 3.1 (2H, s), 3.15 (2H, m), 3.36 (1H, m), 5.1–5.4 (2H, m), 5.74 (1H, d, J 8.5 Hz), 6.48 (1H, m); MS (+ve ion electrospray) m/z 533 (MH$^+$, 85%).

EXAMPLE 50

Mutilin 14-(exo-8-methyl-8-azabicyclo[3.2.1]oct-3-ylsulfanyl)-acetate

The title compound was prepared from endo-8-methyl]-8-azabicyclo[3.2.1]octan-3-ol and mutilin 14-methanesulfonyloxyacetate using the process described in Example 15 0.09 g (17%); $^1$H NMR (CDCl$_3$) inter alia 0.74 (3H, d, J 6.7 Hz), 0.99 (3H, d, J 7.5 Hz), 1.18 (3H, s), 1.63 (3H, s), 2.28 (3H, s), 3.0 (1H, m), 3.13 (2H, s), 3.16 (2H, m), 3.36 (1H, m), 5.15 to 5.37 (2H, m), 5.77 (1H, d, J 8.3 Hz), 6.49 (1H, m); MS (+ve ion electrospray) m/z 518 (MH$^+$, 100%).

EXAMPLE 51

Mutilin 14-[(3-(quinuclidin-4-ylsulfanyl)]-propionate

Step 1. Mutilin 14-acrylate-11-trifluoroacetate

Mutilin 11-trifluoroacetate (WO 97/25309 Example 85 step 2) (3.0 g, 0.0072 mole), triethylamine (3.74 g, 0.037 mole) and a catalytic amount of 4-dimethylaminopyridine in dichloromethane (100 mls) was treated with acryloyl chloride (3.33 g, 0.037 mole) overnight at room temperature under argon. The reaction mixture was partitioned between water and dichloromethane. The organic layer was dried over magnesium sulfate and the solvents removed in vacuo. Chromatography of the residue on silica gel eluting with ethylacetate/petroleum ether 40–60° (1:10) provided the title compound 15 g (37%); $^1$H NMR (CDCl$_3$) inter alia 0.69 (3H, d, J 6.6 Hz), 0.84 (3H, d, J 7 Hz), 1.06 (3H, s), 1.52 (3H, s), 2.1 to 2.4 (4H, m), 2.65 (1H, m), 5.0 (1H, d, 6.9 Hz), 5.20–5.37 (2H, m), 5.72–5.86 (2H, m), 6.0–6.1 (1H, m), 6.3–6.5 (2H, m).

Step 2. Mutilin 14-[(3-quinuclidin-4-ylsulfanyl)]-propionate

Mutilin 14-acrylate-11-trifluoroacetate (0.376 g, 0.008 mole) was treated with preprepared potassium quinuclidin-4-sulfanate from quinuclidin-4-thiol hydrochloride (0.145 g, 0.0008 mole) and potassium tert-butoxide (0.094 g, 0.000838 mole) in ethanol (15 ml) under argon at room temperature overnight. Solvents were removed in vacuo and the residue chromatographed on silica el using chloroform/methanol/35% ammonia solution (10:1:0.1) mixture. This chromatographed product (0.262 g) was dissolved in tetrahydrofuran/water (5:1) (6 ml) and treated with 0.5 M sodium hydroxide solution (1 ml) for 3 hours at room temperature. The reaction mixture was concentrated in vacuo. The residue was chromatographed on silica gel using chloroform/methanol/35% ammonia solution (9:1:0.1) mixture to provide the title compound 0.152 g (36% overall); $^1$H NMR (CDCl$_3$) inter alia 0.72 (3H, d, J 6.5 Hz), 0.87 (3H, d, J 7.0 Hz), 1.08 (3H, s), 1.63 (3H, s), 1.69 (6H, t, J 8 Hz), 2.00–2.47 (7H, m), 2.74 (2H, t, J 7.8 Hz), 3.36 (1H, m), 5.17–5.38 (2H, m), 5.74 (1H, d, J 8.5 Hz), 6.52 (1H, m); MS (+ve ion electrospray) m/z 518 (MH$^+$, 100%).

EXAMPLE 52

Mutilin 14-[3-(quinuclidin-4-ylmethylsulfanyl)]-propionate

To an ice-cooled solution of triphenylphosphine (1.1 g, 0.0042 mole) in dry tetrahydrofuran (50 ml) was added dropwise diisopropyl azodicarboxylate (0.85 g, 0.0042 mole). After 30 mins a solution of thiolacetic acid (0.335 g, 0.0042 mole) and quinuclidin-4-ylmethanol (Example 28, Step 1) (0.565 g. 0.004 mole) in dry tetrahydrofuran (20 ml) was added dropwise. The mixture was stirred under argon for 72 hours, evaporated in vacuo and taken up in ether. The ethereal solution was extracted with 1M hydrochloric acid. The aqueous extract was washed with ether and evaporated to dryness to give a solid (0.65 g). The title compound was prepared from the latter solid and mutilin 14-acrylate-11-trifluoroacetate (Example 51. Step 1) according to the procedure of Example 51. Step 2 0.41 g (80%); $^1$H NMR (CDCl$_3$) inter alia 0.72 (3H, d, J 6.8 Hz), 0.87 (3H, d, J 7 Hz), 1.09(3H, s), 1.45 (3H, s), 1.48 (6H, t, 8 Hz), 2.46 (2H, s), 2.52 (2H, m), 2.75 (2H, m), 2.95 (6H, t, J 7.8 Hz), 3.44 (1H, m), 5.28 (2H, m), 5.75 (1H, d, J 8.5 Hz), 6.52 (1H, m); MS (+ve ion electrospray) m/z 532 (MH$^+$, 100%).

EXAMPLE 53

Mutilin 14-[$^3$-(1-methylpiperid-4-ylsulfanyl)]-propionate

A solution of triphenylphosphine (5.51 g, 0.021 mole) in dry tetrahydrofuran (100 ml) treated with diisopropyl azodicarboxylate (4.25 g, 0.021 mole). After 30 minutes a solution of 1-methylpiperidin-4-ol (2.3 g, 0.02 mole) and thiolacetic acid (1.54 g, 0.02 mole) in dry tetrahydrofuran (50 ml) was added over a period of 30 minutes. The mixture was stirred overnight, concentrated in vacuo and the residue taken up in ether. The ethereal solution was extracted with 1M hydrochloric acid. The aqueous extract was washed with ether, evaporated to dryness and dried in vacuo to give a yellow gum (2.4 g). A portion of the gum (0.252 g) was treated with sodium methoxide (0.120 g) in ethanol and subsequently with mutilin 14-acrylate-11-trifluoroacetate (Example 51, Step 1) (0.376 g) according to the procedure of Example 51, Step 2 to give the title compound 0.3 g (74%); $^1$H NMR (CDCl$_3$) inter alia 0.73 (3H, d, J 6.8 Hz), 0.87 (3H, d, J 7.0 Hz), 1.17 (3H, s), 1.46 (3H, s), 2.18 (2H, m), 2.25 (3H, s), 2.40 (2H, m), 2.51 (1H, m), 2.80 (4H, m), 3.35(1H, m), 5.27 (2H, m), 5.74 (1H, d, 8.3 Hz), 6.52 (1H, m); MS (+ve ion electrospray) m/z 506 (MH$^+$, 100%).

EXAMPLE 54

19,20-Dihydromutilin 14-(1-methylpiperid-4-ylsulfanyl)-acetate

Step 1. 19,20-Dihydromutilin 14-methanesulfanyloxyacetate

The title compound was prepared from 19,20-dihydropleuromutilin (A. Birch et al, *Tertrahedron* (1966) Suppl. 8 part II, 359–387) using the literature process for pleuromutilin (H. Egger and H. Reinshagen, *J. Antibiotics* 29 (9), 915); $^1$H NMR (CDCl$_3$) inter alia 0.71 (3H, d, J 7 Hz), 0.77 (3H, t, 7.5 Hz), 0.95 (3H, d, J 8.5 Hz), 0.97 (3H, s), 1.42 (3H, s), 3.21 (3H, s), 3.42 (1H, m), 4.66 (2H, m), 5.72 (1H, d, 8.2 Hz).

Step 2. 19,20-Dihydromutilin 14-(1-methylpiperidin-4-ylsulfanyl)-acetate

The title compound was prepared from 4-hydroxy-1-methylpiperidine and 19,20-dihydromutilin 14-methanesulfonyloxyacetate using the process described in Example 15 0.42 g (83%); $^1$H NMR (CDCl$_3$) inter alia 0.71 (3H, d, J 6.8 Hz), 0.78 (3H, t, J 7.6 Hz,), 0.94 (3H, d, J 7.6 Hz), 0.97 (3H, s), 1.43 (3H, s), 2.25 (3H, s), 2.42 (1m), 2.81 (2H, m), 3.42 (1H, t, J 6 Hz), 5.63 (1H, d, J 8 Hz), MS (+ve ion electrospray) m/z 494 (MH$^+$, 75%).

EXAMPLE 55

19,20-Dihydromutilin 14-(8-methyl-8-azabicyclo[3.2.1]oct-3-ylmethylsulfanyl)-acetate The title compound was prepared from 19,20)-dihydromutilin 14-methanesulfonyloxyacetate (Example 54, step 1) and 8-methyl-8-azabicyclo[3.2.1]oct-3-ylmethanol using the process described in Example 15, 0.335 g(45%); $^1$H NMR (CDCl$_3$) inter alia 0.71 (3H, d, J 6.5 Hz), 0.79 (3H, t, J 7.3 Hz), 0.93 (3H, d, J 7.0 Hz), 0.97 (3H, s), 1.0 to 2.2 (27H, m), 2.28 (3H, s), 2.41 (1H, m), 3.11 (2H, s), 3.17 (2H, m), 3.42 (1H, m), 5.62 (1H, d, J 8.3 Hz); MS (+ve ion electrospray) m/z 520 (MH$^+$, 60%).

EXAMPLE 56

Mutilin 14-[4-(quinuclidin-4-ylsulfanyl)]-butyrate

Step1. Mutilin 14-(4-bromobutyrate)-11-trifluoroacetate

Mutilin 11-trifluoroacetate (WO 97/25309, Example 85, Step 2) (1.25 , 0.003 mole) and pyridine (0.237 g, 0.003 mole) in dry dichloromethane (20 ml) were treated with 4-bromobutyroyl chloride (0.56 g, 0.003 mole) for 72 hours. The mixture was concentrated in vacuo and the resulting residue chromatographed on silica gel using, dichloromethane, providing the title compound, 1.5 (93%); $^1$H NMR (CDCl$_3$) inter alia 0.72 (3H, d, J 6.7 Hz), 0.83 (3)H, d, J 7 Hz), 1.05 (3H, s), 1.43 (3H, s), 2.62 (1H, t, J 7 Hz), 3.46 (2H, t, J 6 Hz), 5.0 (1H. d, J 6.7 Hz), 5.3 (2H, m), 5.69 (1H, d, J 8 Hz), 6.37 (1H, m); MS (+ve ion electrospray) m/z 532 (MH$^+$, 40%).

Step2. Mutilin 14-[4-(quinuclidin-4-ylsulfanyl)]-butyrate

Quinuclidin-4-thiol hydrochloride (0.359 g, 0.002 mole) in ethanol (10 ml) was treated with sodium methoxide (0.216 g,0.004 mole). After 30 minutes mutilin 14-(4-bromobutyrate) (0.565 g, 0.001 mole) was added and the mixture allowed to stand overnight under argon. The reaction mixture was concentrated in vacuo and the residue partitioned between water and chloroformn. The organic layer was dried over magnesium sulfate and concentrated in vacuo. The residue was chromatographed on silica gel using chloroform/methanol/35% ammonia solution (10:1:0.1) to give title compound, 0.190 g (35%); $^1$H NMR (CDCl$_3$) inter alia 0.71 (3H, d, J 6.5 Hz), 0.87 (3H, d, J 6.8 Hz), 1.16 (3H, s), 1.59 (3H, s), 1.81 (14H, m), 2.06 (2H, t, J 8.5 Hz), 2.49 (2H, t, J 7.3 Hz), 2.94 (6H, t, J 7.3 Hz), 3.35 (1H, m), 5.29 (2H, m), 5.75 (1H, d, J 8.5 Hz), 6.52 (1H, m); MS (+ve ion electrospray) m/z 532 (MH$^+$, 100%).

EXAMPLE 57

1,2-Didehydromutilin 14-(1-methylpiperidin-4-ylmethylsulfanyl)-acetate

Step 1. 1,2-Didehydromutilin 11-dichloroacetate

A solution of 1,2-didehydromutilin (1.41 g. 0.0044 mole) (prepared by analogy to the procedure described for 1,2-didehydropleuromutilin, G. Schulz and H. Berner. *Tetrahedronb*, 1984, 40, 905–17), pyridine (0.56 ml. 0.0066 mole) and N,N-dimethylaminopyridine (0.02 g) in tetrahydrofuran (30 ml) was treated with dichloroacetic anhydride (1.16 g, 0.0048 mole) in tetrahydrofuran (5 ml). After 18 hours the mixture was concentrated in vacuo and the residue partitioned between ethyl acetate and dilute hydrochloric acid. The organic phase was separated, washed with water and brine, dried over magnesium sulphate and the solvent removed in vacuo. Chromatography of the residue on silica gel elutin with 20% ethyl acetate in hexanes gave the title compound (1.3 g, 69%) as a colourless solid; $^1$H NMR (CDCl$_3$) inter alia 4.33 (1H, d, J 7.7 Hz), 4.57 (1H, d, J 7.0 Hz), 5.34 (1H, d, J 11.2 Hz), 5.48 (1H, d, J 17.8 Hz), 5.99 (1s), 6.10(1H, d, 6.1 Hz), 6.11 (1H, dd, J 17.8 and 11.2 Hz), 7.67 (11H, d, J 6.1 Hz).

Step 2. 1,2-Didehydromutilin 11 dichloroacetate-14-chloroacetate

A solution of 1,2-didehydromutilin 11dichloroacetate (1.2 g, 0.0028 mole), pyridine (0.7 ml) and N,N-dimethylaminopyridine (0.01 g) in dichloromethane (10 ml) at 0° C. was treated with chloroacetyl chloride (0.33 ml, 0.0042 mole). After stirring at room temperature for 18 hours the mixture was concentrated in vacuo and the residue partitioned between ethyl acetate and dilute hydrochloric acid. The organic phase was separated, washed with water and brine, dried over magnesium sulphate and the solvent removed in vacuo. Chromatography of the residue on silica gel eluting with 20% ethyl acetate in hexanes gave the title compound (0.7 g, 50%) as a colourless solid; $^1$H NMR (CDCl$_3$) inter alia 0.79 (3H, d, J 6.8 Hz), 1.04 (3H, d, J 7.1 Hz), 1.10 (3H, s), 1.58 (3H, s), 4.00 (2H, s), 4.60 (1H, d, J 7.0 Hz), 5.30 (1H, d, J 17.7 Hz), 5.36 (1H, d, J 11.7 Hz), 5.70 (1H, d, J 8.6 Hz), 5.97 (1H, s), 6.10 (1H, d, J 6.2 Hz), 6.34 (1H, dd, J 17.7 and 11.7 Hz), 7.66 (1H, d, J 6.2 Hz), Step 3. 1,2-Didehydromutilin 11-dichloroacetate-14-(1-methylpiperidin-4-ylmethylsulfanyl)-acetate The title compound (0.36 g, 49%) was prepared from 1,2-didehydromutilin 11-dichloroacetate-14-chloroacetate (0.7 g, 0.0012 mole) and (1-methylpiperidin-4-ylmethylsulfanyl)-acetate (0.224 g, 0.0012 mole) using the process described in Example 39

Step 3. $^1$H NMR (CDCl$_3$) inter alia 0.80 (3H; d, J 6.3 Hz), 1.03 (3H, d, J 7.0 Hz), 1.90 (3H, s), 1.56 (3H, s), 2.26 (3H, s), 3.13 (2H, s), 4.60 (1H, d, J 6.8 Hz), 5.30 (1H, d, J 17.5 Hz), 5.34 (1H, d, J 10.7 Hz), 5.66 (11H, d, J 8.4 Hz), 5.97 (1H, s), 6.09 (1H, d, J 6.1 Hz), 6.34 (1H, dd, J 17.5 and 10.7 Hz), 7.65 (1H, d, J 6.1 Hz); MS (+ve ion electrospray) 616 and 614 (MH$^+$).

Step 4. 1,2-Didehydromutilin 14-(1-methylpiperidin-4-ylmethylsulfanyl)-acetate

A solution of 1,2-didehydromutilin 11-dichloroacetate-14-(1-methylpiperidin-4-ylmethylsulfanyl)-acetate (0.18 g, 0.0003 mole) in dioxane (3 ml) was treated with a aqueous potassium hydroxide (1M, 0.36ml). After stirring at room temperature for 1 hour the mixture was neutralised with dilute hydrochloric acid and the solvent evaporated in vacuo. The residue was partitioned between ethyl acetate and sodium hydrogen carbonate solution. The organic phase was separated, washed with water and brine, dried over magnesium sulphate and the solvent removed in vacuo. Chromatography on silica gel eluting with dichloromethane/methanol/35% ammonia solution (20:1:0.1) gave the title compound (0.12 g, 80%) as a colourless solid: $^1$H NMR (CDCl$_3$) inter alia 0.81 (3H, d, J 6.5 Hz), 1.08 (3H, d, J 7.1 Hz), 1.15 (3H, s), 1.55 (3H, s), 2.26 (3H, s), 3.12 (2H, s), 5.20 (1H, dd, J 17.5 and 1.4 Hz), 5.36 (1dd, J 10.9 and 1.4 Hz), 5.72 (8.6 Hz), 6.04 (1H, d, J 6.1 Hz), 6.47 (1H, dd, J 17.5 and 10.9 Hz), 7.73 (1H, d, J 6.1 Hz); MS (+ve ion electrospray) 504 (MH$^+$).

EXAMPLE 58

Mutilin 14-(exo-8-methyl-8-azabicyclo[3.2.1]oct-3-ylsulfanyl)-acetate

22-Deoxy-22-sulfanylpleuromutilin (U.S. Pat. No. 4,130,709, 1978) (0.1 g, 0.00025 mole) in ethanol (4 ml) was treated with sodium methoxide (0.014 g, 0.0026 mole) and the resulting mixture stirred for 30 minutes. A solution of endo-3-methanesulfonyloxy-8-methyl-8-azabicyclo [3.2.1 ] octane (prepared from endo-8-methyl-8-azabicyclo [3.2.1] octan-3-ol and methanesulfonyl chloride) (0.061 g, 0.00028 mole) in ethanol (1 ml) was then added. Stirring was continued for 68 hours; a further portion of endo-3-methanesulfonyloxy-8-methyl-8-azabicyclo [3.2.1] octane (0.061 g, 0.00028 mole) was then added and stirring continued for a further 18 hours. The mixture was then diluted with dichloromethane, washed twice with aqueous potassium carbonate, once with brine, dried over magnesium sulfate and concentrated in vacuo. Chromatography on silica gel eluting with chloroform/methanol/35% ammonia solution (9:1:0:1) gave the title compound 0.035 g (27%), identical to the compound described in Example 50.

EXAMPLE 59

Mutilin 14-(1-carboxamidomethylpiperidin-4-ylsulfanyl)-acetate

Mutilin (1-carboxymethylpiperidin-4-ylsulfanyl)-acetate (Example 37) (0.08 g, 0.00015 mole) in dichloromethane (3 ml) was treated with oxalyl chloride (0.032 ml, 0.00036 moles) and dimethylformamide (1 drop) and stirred at ambient temperature for 2 hours. The mixture was then evaporated to dryness and the residue suspended in tetrahydofuran (3 ml) and treated with 35% aqueous ammonia solution (25 ml) and stirred for 2 hours. The mixture was evaporated to dryness and the residue positioned between saturated sodium bicarbonate and chloroform. The organic layer was separated and dried (Na$_2$SO$_4$), filtered and evaporated to dryness. Chromatography was saturated on silica gel eluting with chloroform/methanol/35% aqueous ammonia solution (90:9:1). Trituration of the residue obtained with methanol/diethyl ether gave the title compound 0.035 g; M.S. (+ve ion electrospray) m/z 535(MH$^{30}$, 88%).

Antibacterial Activity

The following Table illustrates the antibacterial activities of representative mutilin 14-esters. Activities are given as minimum inhibitory concentrations in micrograms per milliliter ($10^{-6}$ g/ml), and were determined using a standard broth dilution method in microtitre.

| Organism | Pleuromutilin | Tiamulin | Compound from Example 1 | Compound from Example 15 | Compound from Example 50 |
|---|---|---|---|---|---|
| S.a. | 2 | 0.25 | ≦0.06 | ≦0.06 | ≦0.06 |
| S.p. | 8 | 0.25 | ≦0.06 | ≦0.06 | ≦0.06 |
| E.c. | >64 | >64 | 16 | 64 | 32 |
| H.i. | 2 | 2 | 0.25 | 0.5 | 0.5 |
| M.c. | 0.5 | 0.125 | ≦0.06 | ≦0.06 | ≦0.06 |

S.a. = *Staphylococcus aureus* Oxford;
S.p. = *Streptococcus pneumoniae* 1629;
E.c. = *Escherichia coli* DC0;
H.i. = *Haemophilius influenzae* Q1:
M.c. = *Moraxella catarrhalis* Ravasio

PHARMACEUTICAL COMPOSITIONS

Example 1

Oily Spray Formulation

A carrier for a nasal spray formulation was prepared by forming a blend of 67% w/w fractionated coconut oil (medium chain length)* and 33% w/w of glyceryl mono-oleate . To this blend was added 0.2% w/w of powdered lemon juice flavour, followed by 0.5 or 1.0% w/w of drug substance (either in solution or, if insoluble, micronized) *.

Commercial product Miglyol, obtainable from Condea.
Commercial product Mvverol 18-99, obtainable from Eastman.
for example, the compound of Example 1 or Example 8.

The resultant formulation has a viscosity which is sprayable at 20° C. or above. When sprayed into the nose of a patient, the liquid coats the nasal passages and contact with moisture inside the nose (from the mucous membranes, and the humid environment generally) causes the carrier to thicken. This prolongs the residence time of the sprayed formulation on the nasal surfaces. A spray volume of about 100 µl contains approximately 0.5 or 1 mg of drug substance.

Example 2

Aqueous Spray formulation

| Component | % | Purpose |
|---|---|---|
| Drug | 0.001–1.00 | Active |
| Sodium Chloride | 0.5–0.9 | Tonicity modifier |
| Benzalkonium chloride | 0.02 | Preservative |
| Disodium edetate | 0.1 | Part of preservative system/chelating agent |
| Polysorbate 80 | 0.2 | Surfactant/solubiliser |
| Sodium dihydrogen orthophosphate | 0.2 | Buffer |
| Water | qs | Carrier |

Hydrochloric acid and sodium hydroxide were used to adjust the pH of the composition to about pH 5.5. The drug molecule shows optimum stability at this pH.

What is claimed is:

1. A compound of general formula (IA) or (IB):

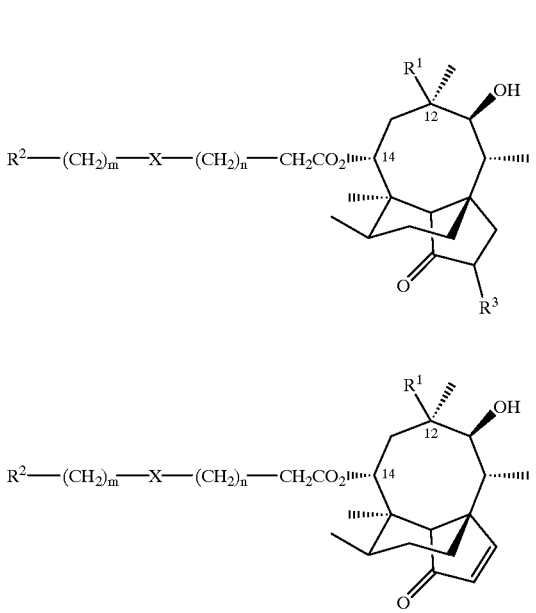

in which:
- each of n and m is independently 0, 1 or 2; and
- X is selected from —O—, —S(O)—, —SO₂—, —CO.O—, —NH—, —CONH—, —NHCONH— and a bond; or
- n is 1 or 2 and m is 2 and X is —S—; and
- $R^1$ is vinyl or ethyl;
- $R^2$ is optionally substituted quinuclidinyl, azabicyclo[2.2.1]heptyl, azabicyclo[4.3.0]nonyl, azabicyclo[3.2.1]octyl, azabicyclo[3,3,0]octyl, azabicyclo[2.2.2]octyl, azabicyclo[3.2.1]octenyl, azabicyclo[3.3.1]nonyl or azabicyclo[4.4.0]decyl;
- $R^3$ is H or OH; or
- the moiety $R^2(CH_2)_m X(CH_2)_n CH_2COO$ at position 14 of (IA) or (IB) is replaced by $R^a R^b C=CHCOO$ in which one of $R^a$ and $R^b$ is hydrogen and the other is $R^2$ or $R^a$ and $R^b$ together form $R^2$; or a pharmaceutically acceptable salt thereof.

2. A compound according to claim 1 in which $R^2$ is substituted by alkyl, alkyloxy, alkenyl or alkenyloxy, which are optionally further substituted by one or more groups selected from aryl, heterocyclyl, ($C_{1-6}$)alkoxy, ($C_{1-6}$)alkylthio, aryl($C_{1-6}$)alkoxy, aryl($C_{1-6}$)alkylthio, amino, mono- or di-($C_{1-6}$)alkylamino, cycloalkyl, cycloalkenyl, carboxy and esters thereof, amides of carboxy, ureido, carbamimidoyl (amidino), guanidino, alkyl-sulfonyl, aminosulfonyl ($C_{1-6}$)acyloxy, ($C_{1-6}$)acylamino, azido, hydroxy, and halogen.

3. A compound according to claim 1 in which n is 0.

4. A compound according to claim 1 in which m is 0 or 1.

5. A compound according to claim 1 in which $R^2$ is quinuclidinyl.

6. A compound according to claim 1 which has the formula (IA).

7. A compound according to claim 1 selected from:
mutilin 14-(quinuclidin-4-yl-sulfanyl)-acetate;
19,20-dihydromutilin 14-(quinuclidin-4-yl-sulfanyl)-acetate;
mutilin 14-(quinuclidin-3-yloxy)-acetate;
mutilin 14-(quinuclidin-3-ylsulfanyl)-acetate;
mutilin 14-(quinuclidin-4-yl-sulfanyl)-acetate;
mutilin 14-[N-(2,2-dimethylazabicyclo[4.3.0]non-4-ylmethyl)]-aminoacetate;
mutilin 14-(quinuclidin-4-ylcarbonylamino)-acetate;
mutilin 14-[(3R,4R)-azabicyclo[2.2.1]hept-3-ylcarbonylamino]-acetate;
mutilin 14-(quinuclid-4-ylmethylsulfanyl)-acetate;
19,20-dihydromutilin 14-(quinuclidin-4-ylsulfonyl) acetate;
19,20-dihydromutilin 14-(quinclidin-4-ylsulfoxy)-acetate;
mutilin 14-{(3RS,4SR)-1-aza-bicyclo[2.2.1]hept-3-ylsulfanyl}-acetate;
mutilin 14-(quinuclidin-3-ylidene)-acetate;
mutilin 14-[quinuclidin-3-yl]-acetate;
mutilin 14-[quinuclidin-3-ylacetoxy]-acetate;
mutilin 14-(quinuclidin-3-ylmethylsulfanyl)-acetate;
1,2-didehydromutilin 14-(quinuclidin-4-ylsulfanyl)-acetate;
2α-hydroxymutilin 14-(quinuclidin-4-ylsulfanyl)-acetate;
mutilin 14-(quinuclidin-4-yl)-acetate;
mutilin 14-(quinuclidin-4-ylmethyl)-aminoacetate;
mutilin 14-[3-(quinuclidin-4-yl)-acrylate;
mutilin 14-[3-(quinuclidin-4-yl)]-propionate;
mutilin 14-(quinuclidin-4-ylmethyloxy)-acetate;
mutilin 14-[(3R)-quinuclidin-3-ylamino]-acetate;
mutilin 14-(quinuclidin-4-yl-amino)-acetate;
mutilin 14-[(3R)-quinuclidin-3-ylamino )]-acetate;
mutilin 14-(quinuclidin-4-yl-amino)-acetate;
mutilin 14-[4-(quinuclidin-4-yl)]-butyrate;
mutilin 14-(1-azabicyclo[3,3,0]oct-4-ylmethylsulfanyl)-acetate;
mutilin 14-(1-azabicyclo[3,3,0]oct-3-ylsulfanyl)-acetate;
mutilin 14-(endo 8-methyl-8-azabicyclo[3,2,1]oct-3-ylsulfanyl)-acetate;
mutilin 14-(1-azabicyclo[4,3,0]non-4-ylsulfanyl)-acetate;
19,20-dihydromutilin 14-(1-azabicyclo[4,3,0]non-4-ylsulfanyl)-acetate;
mutilin 14-{(3S,4R)-1-azabicyclo[2.2.1]hept-3-ylmethylsulfanyl}-acetate;
mutilin 14-(quinuclidin-2-ylmethylsulfanyl)-acetate;
mutilin 14-(1-azabicyclo[2.2.1]hept-4-ylmethylsulfanyl)-acetate;
mutilin 14-{(3R,4S)-1-azabicyclo[2.2.1]hept-3-ylmethylsulfanyl}-acetate;
mutilin 14-(1-azabicyclo[3.2.1]oct-5-ylmethylsulfanyl)-acetate;
mutilin 14-(quinuclidin-4-ylmethylsulfanyl)-acetate;
mutilin 14-(8-methyl-8-azabicyclo [3.2.1]oct-3-ylmethylsulfanyl)-acetate;
mutilin 14-(exo-8-methyl-8-azabicyclo[3.2.1]oct-3-ylsulfanyl)-acetate;
mutilin 14-[(3-(quinuclidin-4-ylsulfanyl)]-propionate;
mutilin 14-[3-(quinuclidin-4-ylmethylsulfanyl)]-propionate;
19,20-dihydromutilin 14-(8-methyl-8-azabicyclo[3.2.1]oct-3-ylmethylsulfanyl)-acetate;

mutilin 14-[4-(quinuclidin-4-ylsulfanyl)]-butyrate; and mutilin 14-(exo-8-methyl-8-azabicyclo[3.2.1]oct-3-ylsulfanyl)-acetate.

8. A process for preparing a compound according to claim 1 which comprises:

(a) coupling mutilin or epi-mutilin having a protected hydroxy group at position 11, with an active derivative, such as an acid chloride, of a carboxylic acid $R^{2A}$—$(CH_2)_m$—X—$(CH_2)_n$—$CH_2CO_2H$, where $R^{2A}$ is $R^2$ as defined in claim 1 or a group convertible thereto, and n, m, and X are as defined in claim 1, and if necessary converting the epi-mutilin to mutilin, and where necessary or desired, before or after the coupling, modifying the mutilin nucleus to introduce 2—OH; 19,20-dihydro; or 1,2-dehydro substituents; or (b) providing a mutilin or epi-mutilin drivative having $(CH_2)_nCH_2CO$ as an O-acyl group at position 14, where the acyl group is substituted with $R^L$, which is a leaving group, OH or NH, coupling the 14-O-acyl-(epi) mutilin derivative with a compound $R^{2A}(CH_2)_mXH$ or an active derivative therof, and if necessary converting the epi-mutilin configuration to mutilin, and where necessary or desired, before or after the coupling, modifying the mutilin nucleus to introduce 2-OH; 19,20-dihydro; or 1,2-dehydro substituents.

9. A process for preparing a compound according to claim 8(b) in which (a) when X is O, S or NH, $R^L$ is a leaving group and is reacted with (i) the alcohol $R^2$—$(CH2)_m$—OH;

(ii) the thiol $R^2$—$(CH_2)_m$—SH;

(iii) the amine $R^2$—$(CH_2)_m$—$NH_2$;

(b) when X is CONH, $R^L$ is amino and is reacted with the acid $R^{2A}$—$(CH_2)_m$—$CO_2H$, or an acylating agent derived therefrom;

(c) when X is CO.O, $R^L$ is hydroxy and is reacted with an acylating agent derived from the acid $R^{2A}$—$(CH_2)_m$—$CO_2H$.

10. A pharmaceutical composition comprising a compound according to claim 1 and a pharmaceutically acceptable carrier.

11. A pharmaceutical composition according to claim 10 in the form of a spray adapted for administration to the nasal cavity.

12. A pharmaceutical composition according to claim 11 in which the spray is an aqueous spray.

13. A method of treating bacterial infection which method comprises administering an anti-bacterial effective amount of a compound of formula (IA) or (IB) according to claim 1 to a patient in need thereof.

14. A method of reducing or eliminating the nasal carriage of pathogenic organisms which method comprises administering an effective amount of a compound of formula (IA) or (IB) according to claim 1 to a patient in need thereof.

15. A method of prophylaxis of recurrent otitis media or recurrent acute bacterial sinusitis which comprises administering an effective amount of a compound of formula (IA) or (IB) according to claim 1 to a patient in need thereof.

* * * * *